United States Patent [19]
Oefner et al.

[11] Patent Number: 5,795,976
[45] Date of Patent: Aug. 18, 1998

[54] DETECTION OF NUCLEIC ACID HETERODUPLEX MOLECULES BY DENATURING HIGH-PERFORMANCE LIQUID CHROMATOGRAPHY AND METHODS FOR COMPARATIVE SEQUENCING

[75] Inventors: Peter Josef Oefner, Innsbruck, Austria; Peter Anton Underhill, Palo Alto, Calif.

[73] Assignee: The Board of Trustees of the Leland Stanford Junior University, Stanford, Calif.

[21] Appl. No.: 512,681

[22] Filed: Aug. 8, 1995

[51] Int. Cl.⁶ .............. C12N 15/10; C07H 21/02; C12Q 1/68; C12P 19/34
[52] U.S. Cl. ............ 536/25.4; 536/22.1; 536/23.1; 536/24.3; 435/6; 435/91.2; 204/450; 204/456; 204/182.8
[58] Field of Search .............. 435/6, 5, 91.2, 435/91.5; 536/24.3, 24.31, 24.32, 24.33, 25.4; 204/450, 456, 182.8

[56] References Cited

U.S. PATENT DOCUMENTS 4,683,195  7/1987  Mullis et al.
4,965,188  10/1990  Mullis et al.

FOREIGN PATENT DOCUMENTS

WO 94/11305  5/1994  WIPO

OTHER PUBLICATIONS

Agius, G., et al., "Variable Stringency Hybridization of Polymerase Chain Reaction Amplified HIV-1 DNA Fragments," *J. Virol. Meth.* 30:141–150 (1990).

Clay T.M., et al., "PCR-Fingerprinting for Selection of HLA Matched Unrelated Marrow Donors," *The Lancet* 337(8749):1049–1052 (1991).

Cotton, R.G.H., "Detection of Mutations in DNA," *Current Opin. in Biotechnol.* 3:24–30 (1992).

Cotton, R.G.H., "Current Methods in Mutation Detection," *Mutation Res.* 285:125–144 (1993).

Huber, C.G., et al., "Rapid and Accurate Sizing of DNA Fragments by Ion–Pair Chromatography on Alkylated nonporous Poly (styrene–divinylbenzene) Particles," *Anal. Chem.* 67:578–585 (1995).

Jin, L., et al., "Systematic Search for Polymorphisms in the Human Genome Using Denaturing High–Performance Liquid Chromatography (DHPLC)," *Am. J. Human Genet.* 57:A26 (Oct. 1995).

Kellogg, D.E., et al., "Quantitation of HIV-1 Proviral DNA Relative to Cellular DNA by the Polymerase Chain Reaction," *Anal. Biochem.* 189:202–208 (1990).

Oefner, P.J., et al., "High Resolution Liquid Chromatography of Fluorescent Dye-Labeled Nucleic Acids," *Anal. Biochem.* 223:39–46 (1994).

Oefner, P.J., et al., "High–Performance Liquid Chromatography for Routine Analysis of Hepatitis C Virus cDNA/PCR Products," *Res. Reports* 16:5 (1994).

Oefner, P., and Underhill, P.A., Comparative DNA Sequencing by Denaturing High–Performance Liquid Chromatography (DHPLC), *Am. J. Human Genet.* 57:A266 (Oct. 1995).

Underhill, P.A., et al., "Y–Chromosomal Variation and Recent Conquests in Deciphering Human Origins," *Am. J. Human Genet.* 57:A43 (Oct. 1995).

Zemans, R., et al., "Identification and Characterization of Pre–Columbian Human Y Chromosome Specific Allele," *Am. J. Human Genet.* 57:A174 (Oct. 1995).

Nagamine et al, "A PCR Artifact: Generation of heteroduplexes", Am. J. Hum. Genet. 45:337–339, 1989.

Prost et al, "The polymerase chain reaction and its applications", Meth. Mol. Cell. Biol. 1(2):45–51, Mar. 1989.

Keen et al, "Rapid detection of single base mismatches as heteroduplexes on hydrolink gels", Trends Genet. 7(1):5, Jan. 1991.

Hayward–Lester et al, "Rapid quantification of gene expression by competitive RT–PCR and Ion–pair reversed phase HPLC", Biotechniques 20(2):250–257, Feb. 1996.

*Primary Examiner*—W. Gary Jones
*Assistant Examiner*—Jeffrey Fredman
*Attorney, Agent, or Firm*—Susan T. Evans; Gary R. Fabian

[57] ABSTRACT

The present invention describes a method for separating heteroduplex and homoduplex DNA molecules in a mixture. In the method, such a mixture is applied to a stationary reverse phase support. The heteroduplex and homoduplex molecules are eluted with a mobile phase containing an ion-pairing reagent and an organic solvent. The eluting is carried out under conditions effective to at least partially denature the heteroduplexes (e.g., thermal or chemical denaturing) resulting in the separation of the heteroduplexes from the homoduplexes. The method has many applications including, but not limited to, comparative nucleic acid sequencing, linkage analysis, evolutionary studies, forensics, identification of disease-causing gene mutations, genetic marker development and diagnostics.

20 Claims, 14 Drawing Sheets

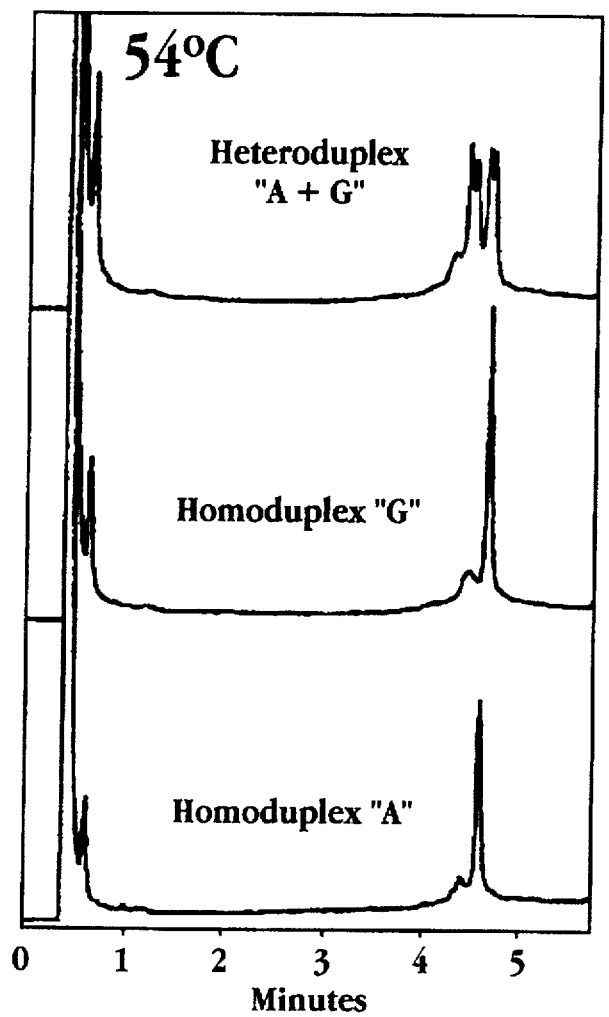

DETECTION OF NUCLEIC ACID HETERODUPLEX MOLECULES BY DENATURING HIGH-PERFORMANCE LIQUID CHROMATOGRAPHY AND METHODS FOR COMPARATIVE SEQUENCING

FIELD OF THE INVENTION

The present invention relates to a chromatographic method for detecting heteroduplexes in nucleic acid fragments, and particularly to denaturing high performance liquid chromatography, for use in detecting mutations and for comparative DNA sequencing.

References

Bayever, E., et al., *Antisense Research and Development* 3:383–390 (1993).
Bowman, et al., *Mol. Biol. and Evolution* 9:893–904 (1992).
Breniere, et al., *Am. J. Trop. Med. and Hygiene* 46:335–41 (1992).
Briones, et al., *Mol. and Bio. Parasitology* 53:121–7 (1991).
Calabretta, B., et al., *Seminars in Cancer Biol.* 3(6):391–398 (1992).
Calabretta, B., et al., *Cancer Treatment Rev.* 19(2):169–179 (1993).
Cox, et. al., *Science* 265:20–31 (1994).
Bonn, G., et al., PCT International Publication No. WO 94/11305, published 26 May 1994.
Crea, R., U.S. Pat. No. 4,888,286, issued Dec. 19, 1989.
D'Aquila, R. T., et al., *Nucleic Acids Research* 19:3749 (1991).
Don, R. H., et al., *Nucleic Acids Research* 19:4008 (1991).
Eaton, M. A. W., et al., U.S. Pat. No. 4,719,180, issued Jan. 12, 1988.
Ellis, et al., *Mol. and Bio. Parasitology* 54:87–95 (1992).
Eriksson, S., et al., *J. Chromatography* 359:265–274 (1986).
Ferre, F., et al., *Aids* 7(Suppl 2):S21–27 (1993).
Gazdar, A. F., et al., U.S. Pat. No. 4,892,829, issued Jan. 09, 1990.
Ghossein, R. A., et al., *Diagnostic Mol. Pathol.* 1(3):185–191 (1992).
Jeffreys, A. J., et al., *Nature* 314:67–73 (1985).
Kawasaki, E. S., et al., in *PCR TECHNOLOGY: PRINCIPLES AND APPLICATIONS OF DNA AMPLIFICATION* (H. A. Erlich, ed.) Stockton Press (1989).
Kleemola, et al., *Pediatric Infect. Dis. J.* 12:344–5 (1993).
Mullis, K. B., U.S. Pat. No. 4,683,202, issued 28 Jul. 1987.
Mullis, K. B., et al., U.S. Pat. No. 4,683,195, issued 28 Jul. 1987.
Myers, R. M., et al., *Science* 230:1242–1246 (1985).
Myers, R. M., et al., *Science* 232:613–618 (1986).
Sambrook, J., et al., In *MOLECULAR CLONING: A LABORATORY MANUAL*, Cold Spring Harbor Laboratory Press, Vol. 2 (1989).
Seielstad, M. T., et al., *Human Molecular Genetics* 3:2159–2161 (1994).
Ugelstad, J., et al., *Adv. Colloid Interface Sci.* 13:101–140 (1980).
Vohra, et al., *J. Mol. Eval.* 34:303–395 (1992).
Volkenandt, M., et al., *Proc. Soc. Exp. Biol. Med.* 200:1–6 (1992).
Vollrath, D. et al., *Science* 258:52–59 (1992)
Wang, A. M., et al. in *PCR PROTOCOLS: A GUIDE TO METHODS AND APPLICATIONS* (M. A. Innis, et al., eds.) Academic Press (1990).
Weber, J. et al., *Am. J. Hum. Genet.* 44:388–396 (1989).
Weisburg, W. G., et al., *J. Bacteriology* 171(12):6455–6467 (1989).
Weiss, et al., *Mol. & Bioch. Parasitology* 54:72–86 (1992).
Wickstrom, E., Editor, *PROSPECTS FOR ANTISENSE NUCLEIC ACID THERAPY OF CANCER AND AIDS*, Wiley-Liss, New York, N.Y. (1991).
Wolfe, K. H., et al., *Plant Molec. Biol.* 18(6):1037–1048 (1992).
Yoshio, T., et al., U.S. Pat. No. 4,849,350, issued Jul. 18, 1989.
Zalewski, A., et al., *Circulation Res.* 88:1190–1195 (1993).
Zimmerman, et al., *Mol. & Bioch. Parasitology* 58:259–267 (1993).

BACKGROUND OF THE INVENTION

The deciphering of the genetic code and the establishment of the structure of deoxyribonucleic acid (DNA) in the early 1960s initiated a revolution in modern biology. Since that time, numerous methods have been developed for the isolation, analysis and manipulation of nucleic acid molecules.

DNA is a double-stranded polynucleotide composed of two polynucleotide strands that are oriented in opposite directions (i.e., the strands are anti-parallel). Each nucleotide is composed of a nitrogenous base, a deoxyribose sugar molecule and a phosphate group. The nucleotides are linked together by phosphodiester bonds in which a phosphate group connects the 5' carbon atom of one deoxyribose to the 3' carbon of the deoxyribose in an adjacent nucleotide to form the DNA backbone. The two strands are held together by hydrogen bonding interactions between complementary bases on opposing chains.

A normal human being possesses 23 pairs of chromosomes containing a total of about 70,000 genes. The length of DNA contained within the human chromosomes totals about 3.3 billion base pairs, with a typical gene containing about 30,000 base pairs.

Due to the vast amount of genetic information yet to be gathered in both human and non-human genomes, intense efforts are underway to develop new and faster methods of DNA detection, sizing, quantification, sequencing, and gene identification including the mapping of human disease genes. Although the efficiency of these processes has been improved by automation, more efficient and less expensive methods must still be developed to efficiently carry out genomic-scale DNA analyses.

The majority of DNA in higher organisms is identical in sequence among the chromosomes of different individuals. However, a small fraction of DNA is variable or polymorphic in sequence. It is this variation which is the essence of genetic science and human diversity. Customary analysis of DNA polymorphisms relies on variations in the lengths of DNA fragments produced by restriction enzyme digestion. The polymorphisms identified using this approach are typically referred to as restriction fragment length polymorphisms or RFLPs. Polymorphisms involving variable numbers of tandemly repeated DNA sequences between restriction enzyme sites, typically referred to as microsatellites or variable numbers of tandem repeats (VNTRs) have also been identified (Jeffreys, et al.). Other tandemly repeated DNA motifs, different in sequence from the Jeffreys' VNTRs are also known to exist. In one such set of genetic markers, the microsatellites consist of DNA fragments typically about 300 base pairs or fewer in length and containing one or more blocks of tandem dinucleotide repeats $(dC-dA)_n \cdot (dG-dT)_n$, where the number of dinucleotide repeat units is typically six or greater (Weber, et al.).

Mutations arise during replication as a change in the sequence of a gene, with different mutations having differing consequences. For example, some mutations occur in the coding region. A nonsense mutation is a mutation resulting from a point mutation that converts a codon to a stop codon, producing a premature termination of the polypeptide chain and typically resulting in production of a nonfunctional protein. Base substitutions may or may not result in the incorporation of an incorrect amino acid in a resulting protein, due to the redundancy of the genetic code. A missense mutation (resulting from incorporation of an incorrect amino acid) may have little effect on the function of the protein produced unless it occurs in a critical region of the protein.

In fact, single base pair changes are frequent in the human genome. The level of genetic variation between two individual sequences is estimated to be on average one difference per 1,000 base pairs. Based on this estimate, the average amount of genomic variation between individuals is about 3 million base pairs. It is this normal polymorphism which provides the basis for some of the existing gene localization strategies.

The detection of polymorphisms is becoming increasingly important, particularly in gene mapping. Reference markers are often selected for their high degree of polymorphism, so that they may be used for linkage analysis in family pedigrees. The most commonly used polymorphic PCR compatible markers are microsatellites which can localize genes to several million base pairs. Further localization by microsatellites is hindered, however, by their relatively high mutation rate.

As the sequences of greater numbers of genes are identified, the detection of specific polymorphisms in such genes and the correlation to specific diseases can provide an invaluable tool in the screening and detection of diseases. Diagnostic screening methods for polymorphisms are also useful in the detection of inherited diseases in which either a single point mutation or a few known mutations account for all cases (e.g., sickle cell disease). Presently, over 200 genetic disorders can be diagnosed using recombinant DNA techniques, and such techniques have also been used for other purposes, such as for forensic screening.

Presently used methods for screening for polymorphic sites within a gene include RNase A cleavage, chemical cleavage, denaturing gradient gel electrophoresis. These methods exploit characteristics of mismatched heteroduplexes formed between normal and mutant sequences.

RNase cleavage uses the enzyme ribonuclease A to cut RNA-DNA hybrids wherever there is a mismatch between a nucleotide in the RNA strand and the corresponding nucleotide in the DNA strand. Using this method, a radioactive RNA probe is produced by using the normal sequence cloned in a vector with a phage RNA polymerase gene. The RNA strand anneals to the test genomic DNA and the mixture is treated with RNase A. If the DNA contains a mutation, then the enzyme cuts the RNA strand and two radioactive RNA fragments are detected on a denaturing gel. If the test DNA is normal, then a single RNA fragment corresponding to the intact RNA probe is detected. Typically, about 70% of mutations are detected using this method (Myers, et al., 1985).

The chemical cleavage method is based upon a similar principle but uses hydroxylamine and osmium tetroxide to distinguish between mismatched C or T nucleotides, respectively. The position of the mismatch (e.g., the mutation) is defined by sizing on gel electrophoresis after cleavage at the reactive position by piperidine.

In denaturing gradient gel electrophoresis (DGGE), either homoduplex or heteroduplex double stranded DNA is electrophoresed under denaturing conditions of increasing concentration until the last domain is denatured, and migration of the DNA through the gel is retarded. DNA sequences differing by a single base pair migrate at different rates along the gel, thereby allowing detection of a polymorphic site, if present.

Another analytical method for screening for polymorphisms is single-stranded conformation polymorphism or SSCP. Utilizing this technique, DNA is denatured and then immediately run on a non-denaturing gel. The secondary structures of wild-type strands or mutant single strands differing by a single base are usually sufficiently different to result in different migration rates on polyacrylamide gels.

Allele-specific oligonucleotide probes (or ASOs) are probes that are designed to hybridize selectively to either a normal or a mutant allele. These probes can be used for detecting a polymorphism in which the nucleotide sequence of the mutant and normal alleles are known. In this technique, probes are developed to distinguish between the normal and mutant sequence by altering the stringency of hybridization to a level at which each of the oligonucleotides will anneal stably only to the sequence to which it is perfectly complementary and not to the sequence with which it has the single mismatch. In using this technique, stringent hybridization conditions are necessary to distinguish a single base-pair mismatch.

The ligase-mediated method for detecting mutations makes use of the fact that the ends of two single strands of DNA must be exactly aligned for DNA ligase to join them. In utilizing this technique, oligonucleotides complementary to the target sequence, 5' to and including the mutation site, are synthesized and labeled. A third oligonucleotide complementary to the common sequence 3' to the mutation site is synthesized and also labeled. The oligonucleotides are then hybridized to strands of the target. In cases in which the 5' and 3' oligonucleotides form a flush junction that can be joined by DNA ligase, ligation occurs. However, a single base pair mismatch occurring between the normal 5' oligonucleotide and the mutation site is sufficient to prevent the ligase from acting and can readily be detected.

Existing methods for locating polymorphic sites, point mutations, insertions and deletions on a gene are generally time consuming, necessitate multiple handling steps, require product purification, are not readily adaptable to automation, and are typically limited to detection in small-sized nucleic acid fragments.

SUMMARY OF THE INVENTION

The present invention provides a method for separating heteroduplex and homoduplex nucleic acid molecules (e.g., DNA or RNA) in a mixture using high performance liquid chromatography. In the separation method, a mixture containing both heteroduplex and homoduplex nucleic acid molecules is applied to a stationary reverse-phase support. The sample mixture is then eluted with a mobile phase containing an ion-pairing reagent and an organic solvent. Sample elution is carried out under conditions effective to at least partially denature the heteroduplexes and results in the separation of the heteroduplex and homoduplex molecules.

Stationary phases for carrying out the separation include reverse-phase supports composed of alkylated base materials, such as silica, polyacrylamide, alumina, zirconia, polystyrene, and styrene-divinyl copolymers. Styrene-divinyl copolymer base materials include copolymers composed of i) a monomer of styrene such as styrene, alkyl-substituted styrenes, α-methylstyrene, or alkyl substituted α-methylstyrenes and ii) a divinyl monomer such as divinylbenzene or divinylbutadiene. In one embodiment, the surface of the base material is alkylated with hydrocarbon chains containing from about 4–18 carbon atoms. In another embodiment, the stationary support is composed of beads from about 1–100 microns in size.

In the present method, the mobile phase contains an ion-pairing agent and an organic solvent. Ion-pairing agents for use in the method include lower primary, secondary and tertiary amines, lower trialkylammonium salts such as triethylammonium acetate and lower quaternary ammonium salts. A preferred tertiary amine is triethyl amine. Typically, the ion-pairing reagent is present at a concentration between about 0.05 and 1.0 molar. Organic solvents for use in the method include solvents such as methanol, ethanol, 2-propanol, acetonitrile, and ethyl acetate.

In one embodiment, the mobile phase for carrying out the separation of the present invention contains less than about 40% by volume of an organic solvent and greater than about 60% by volume of an aqueous solution of the ion-pairing agent. In a preferred embodiment, elution is carried out using a binary gradient system.

At least partial denaturation of heteroduplex molecules can be carried out several ways including the following. Temperatures for carrying out the separation method of the invention are typically between about 50° and 70° C., preferably between about 55°–65° C. In a preferred embodiment, the separation is carried out at 56° C. Alternatively, in carrying out a separation of GC-rich heteroduplex and homoduplex molecules, a higher temperature (e.g., 64° C.) is preferred.

Alternately, sample elution is carried out under pH conditions effective to at least partially denature the heteroduplex molecules. In such cases, a lower column temperature less than about 65° C. may be sufficient for the separation of the heteroduplex and homoduplexes molecules in the sample.

In the separation method of the present invention, the pH of the mobile phase will vary depending upon the nature and concentrations of various components, and is typically maintained between about 7 and 9. In a preferred embodiment, the mobile phase is maintained at a pH of 7.5, to obtain improved sample resolution.

In one particular embodiment of the present method, homoduplex and heteroduplex molecules in a mixture are separated by applying the mixture to a C-18 alkylated polystyrene-divinylbenzene copolymer stationary support and eluting the mixture with a mobile phase containing triethylammonium acetate as the ion-pairing reagent and acetonitrile as the organic solvent at a temperature between about 50°–65° C.

In an alternate embodiment, the homoduplex and heteroduplex molecules contained in the mixture are amplified using the polymerase chain reaction and the amplified DNA molecules are denatured and renatured to form a mixture of heteroduplex and homoduplex molecules prior to carrying out the separation method of the invention.

Also disclosed is a method for developing new genetic markers for use in mapping genes. In this aspect, a physically mapped DNA fragment (e.g., sequence tagged sites or expressed sequence tags) from various individuals is amplified and any polymorphic site contained therein is identified using the separation method of the present invention. The positions in the genetic map of any such identified polymorphic markers are then assigned by methods which include linkage analysis and determination of the physical distance of the polymorphic marker from other previously genetically mapped markers such as microsatellites.

Using the above aspect of the invention, a collection of polymorphic genetic markers can be provided which are more densely populated and evenly distributed for use in traditional pedigree-based linkage analysis in gene mapping. Such collections of markers can be compiled into index marker sets, e.g., for a selected autosome or sex chromosome. In one embodiment, a selected set of physically mapped sequence tag site and/or expressed sequence tag markers corresponding to a chromosome of interest are screened by the method of the present invention. Markers having polymorphisms are identified. Primers or probes corresponding to the polymorphic markers are then assembled into a marker panel kit for the chromosome of interest. Genetic markers, such as those provided by the methods disclosed herein, are well-distributed across the genome and are low-mutating.

Also disclosed is a method for comparative DNA sequencing in which potentially all possible nucleotide mismatches and insertion/deletions within select amplified DNA fragments obtained from multiple animal or human subjects can be detected. In the context of the present invention, comparative DNA sequencing is carried out by amplifying DNA samples, typically up to at least about 1.5 kb in length, obtained from multiple subjects. The amplified DNA fragments are then surveyed, either individually or in pools containing up to about 10 samples, for the presence or absence of heteroduplexes using the denaturing high performance liquid chromatography method of the present invention.

In surveying the samples, the amplified DNA fragments are denatured and allowed to reanneal. The resulting mixture of DNA fragments is then applied to a stationary reverse-phase support. The sample mixture is eluted with a mobile phase containing an ion-pairing reagent and an organic solvent. Sample elution is carried out under conditions effective to at least partially denature any heteroduplexes present in the sample and results in the detection of any heteroduplex molecules contained in the sample. The detection of a heteroduplex indicates the presence of a base pair mismatch and/or an insertion/deletion in the sample fragment(s).

In instances in which only homoduplexes are observed during the sample screening, further standard sequencing is not required since the sequence is monomorphic (i.e., lacking a polymorphic site) in all subjects compared. In utilizing the method of the present invention, only those DNA fragments identified as heteroduplexes, and therefore identified as containing at least one polymorphic site, are then sequenced by conventional methods to characterize the observed polymorphism(s).

These and other objects and features of the invention will become more fully apparent when the following detailed description is read in conjunction with the accompanying figures and examples.

BRIEF DESCRIPTION OF THE FIGURES

FIGS. 7A-7C are IP-RP-HPLC chromatograms of samples identical to those described for FIGS. 6A-6C above, with the exception that the chromatographic separation was carried out at a column temperature of 54° C.;

FIGS. 8A and 8B are chromatograms of each of the two different 439-mer homoduplexes designated as "homo-A-439" and "homo-G-439 ", respectively, prior to mixing, denaturing, and reannealing;

FIG. 9C illustrates the detection, at 56° C., of two 1-kilobase heteroduplexes, each containing a single base-pair mismatch, in a mixture also containing two 1-kilobase homoduplexes;

FIG. 10-10C are IP-RP-HPLC chromatograms illustrating the separation of 209-base pair homoduplexes from 209-base pair heteroduplexes as a function of column temperature;

DETAILED DESCRIPTION OF THE INVENTION

I. Definitions

Figure 1A:
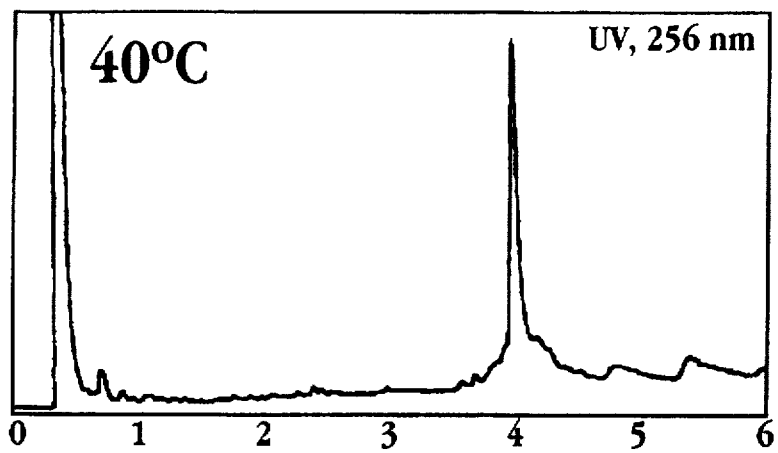
FIGS. 1A–1C are chromatograms resulting from ion-pair reverse-phase (IP-RP) HPLC on a nonporous alkylated poly(styrene-divinylbenzene) solid support maintained at 40° C. for a single stranded 30-mer oligonucleotide (FIG. 1A), a complementary 32-mer oligonucleotide (FIG. 1B), and an equimolar mixture of both the 30-mer and 32-mer (FIG. 1C)

The following terms, as used herein, have the meanings as indicated.

"Reverse phase support" refers to any stationary support (including the base material and any chemically bonded phase) for use in high performance liquid chromatography (HPLC) which is less polar (e.g., more hydrophobic) than the starting mobile phase.

"Ion-pair (IP) chromatography" as used herein refers to any chromatographic method for separating samples in which some or all of the sample components contain functional groups which are ionized or are ionizable. Ion-pair chromatography is typically carried out with a reverse phase column in the presence of an ion-pairing reagent.

"Ion-pairing reagent" is a reagent which interacts with ionized or ionizable groups in a sample to improve resolution in a chromatographic separation. As used herein, ion-pairing agent refers to both the reagent and aqueous solutions thereof. An ion-pairing agent is typically added to the mobile phase in reverse phase HPLC for optimal separation. The concentration and hydrophobicity of an ion-pairing agent of choice will depend upon the number and types (e.g., cationic or anionic) of charged sites in the sample to be separated.

"Alkylated" as used herein in reference to the solid support refers to attachment of hydrocarbon chains to the surface of the base material of the solid support, typically ranging about 3 to 22 carbon atoms in length. The hydrocarbon chains may be saturated or unsaturated and may optionally contain additional functional groups attached thereto. The hydrocarbon chains may be branched or straight chain and may contain cyclic groups such as cyclopropyl, cyclopropyl-methyl, cyclobutyl, cyclopentyl, cyclopentylethyl, and cyclohexyl. Typically, an alkylated solid support refers to an extent of alkylation of the base material of greater than about 50 percent.

"Lower alkyl" refers to an alkyl radical of one to six carbon atoms, as exemplified by methyl, ethyl, n-butyl, i-butyl, t-butyl, isoamyl, n-pentyl, and isopentyl.

"Ion pairing reverse phase high performance liquid chromatography (IP-RP-HPLC)" refers to a type of high performance liquid chromatography in which the solid support is a reverse phase support and the mobile phase contains an ion-pairing reagent.

"Nonporous stationary support" as used herein refers to a solid support composed of a packing material having surface pores of a diameter that excludes permeation of sample compounds into the pore structure, typically of less than about 30 angstroms in diameter.

"Organic solvent" as used herein, refers to a component of the mobile phase utilized in reverse phase ion pairing HPLC. The organic solvent, occasionally referred to as an organic modifier, is any organic (e.g., non-aqueous) liquid suitable for use in the chromatographic separation methods of the present invention. Generally, the organic solvent is a polar solvent (e.g., more polar than the stationary support) such as acetonitrile or methanol.

"Homoduplex molecules" are typically composed of two complementary DNA strands.

"Heteroduplex molecules" are typically composed of two complementary nucleic acid strands (e.g., DNA or RNA), where the strands have less than 100% sequence complementarity. The functional definition of homoduplex and heteroduplex molecules, in the context of the present invention, is apparent from the results presented below. Typically, in a mixed population of homoduplex and heteroduplex molecules, for shorter strands (e.g., typically about less than 70 base pairs in size) heteroduplex molecules elute as peaks corresponding to their respective denatured single strands under select denaturing conditions using reverse phase ion pairing HPLC, separable from those of homoduplex molecules. In a mixed population of homoduplex and heteroduplex molecules larger than about 70 base pairs in length, heteroduplex molecules typically elute with shorter retention times than those of homoduplexes of essentially the same size under select denaturing conditions using reverse phase ion pairing HPLC. "Insertions or deletions" or "indels" can occur in duplexes consisting of two complementary DNA strands, where the first strand of the DNA contains a greater number of nucleotides at an internal site than the second strand DNA molecule, and where these extra nucleotides are flanked by paired-complementary sequences. Indels can occur in heteroduplexes.

"Base-pair mismatches" typically refers to a single base-pair mismatch flanked by matched base-pairs. Base-pair mismatches also include a series of mismatched base-pairs flanked by matched base-pairs. Base-pair mismatches can occur in heteroduplexes.

A heteroduplex molecule that is "at least partially denatured" under a given set of chromatographic conditions refers to a molecule in which several complementary base pairs of the duplex are not hydrogen-bond paired, such denaturing typically extending beyond the site of the base-pair mismatch contained in the heteroduplex, thereby enabling the heteroduplex to be distinguishable from a homoduplex molecule of essentially the same size. In accordance with the present invention, such denaturing conditions may be either chemically (e.g., resulting from pH conditions) or temperature-induced, or may be the result of both chemical and temperature factors.

"Comparative DNA sequencing" as used herein refers to a method for detecting any, and preferentially all, possible nucleotide mismatches and insertion/deletions within select amplified or non-amplified DNA fragments obtained from multiple animal or human subjects. In comparative DNA sequencing, DNA samples, typically up to at least about 1.5 kb in length, are obtained from multiple subjects and amplified or are otherwise produced (e.g., by cloning). The amplified DNA fragments are then surveyed, either individually or in pools containing up to about 10 unique samples, for the presence or absence of heteroduplexes. The detection is of a heteroduplex indicates the presence of a base pair mismatch and/or an insertion/deletion in the sample fragment(s). Although comparative sequencing can be carried out using any of a number of analytical methods, it is particularly suited to the denaturing high performance liquid chromatography method of the present invention.

In the context of the present invention, in instances in which only homoduplexes are observed during the sample screening, further standard sequencing is not required since the sequence is monomorphic in all subjects compared. In utilizing the method of the present invention, only those DNA fragments identified as heteroduplexes, and therefore identified as containing at least one polymorphic site, are sequenced by conventional methods to characterize the observed polymorphism(s).

A "sequence-tagged site" or STS is a short (typically about 200–300 bp long) segment of a human chromosomal DNA molecule whose sequence (i) has been determined and (ii) is known to be unique because the STS can be selectively amplified by specific primers using the polymerase chain reaction. A set of STSs located on a chromosomal DNA molecule can be utilized to integrate the genetic-linkage and physical maps of the chromosomal DNA molecule.

An "expressed sequence tag" or EST is derived from cDNA sequence and is similar to an STS. In addition, it is a sequence known to be expressed (i.e., at least transcribed and most likely translated). ESTs can be used to create an "expression" map by adding the locations of the genes themselves to the physical maps.

II. Denaturing High Performance Liquid Chromatography

The present invention provides a method for separating heteroduplex and homoduplex DNA molecules in a mixture using high performance liquid chromatography and more particularly, denaturing high performance liquid chromatography, as will be described in detail below. The method can be utilized for detecting a single base mismatch in a DNA duplex containing up to about 2000 base pairs.

High performance liquid chromatography (HPLC) generally refers to a technique for partitioning a sample or more specifically the components of a sample between a liquid moving or mobile phase and a solid stationary phase. In the present invention, the applicants have discovered a chromatographic method which utilizes conditions effective for at least partially denaturing heteroduplexes during sample elution to thereby enable the separation and identification of heteroduplexes and homoduplexes contained in a mixture.

A. Stationary Phase

In the method of the present invention, a sample mixture containing both heteroduplex and homoduplex molecules is applied to a stationary phase. Generally, the stationary phase is a reverse phase material in which the chemically bonded phase is hydrophobic and is less polar than the starting mobile phase. Any of a number of commercially available reverse phase solid supports may be utilized in the present nucleic acid separation method although the resolution may vary depending upon the nature of the sample and other relevant experimental parameters.

Reverse phase columns or column packing materials for use in the invention are typically composed of alkylated polymeric base materials such as silica (Eriksson, et al.), cellulose and cellulose derivatives such as carboxymethylcellulose, alumina, zirconia, polystyrene, polyacrylamide, polymethylmethacrylate, and styrene copolymers. In a preferred embodiment, the polymeric base material is a styrene-divinyl copolymer.

Styrene-divinyl copolymers for use as stationary phase base materials include copolymers formed from (i) a styrene monomer such as styrene, lower alkyl substituted styrene (in which the benzene ring contains one or more lower alkyl substituents), α-methylstyrene and lower alkyl α-methylstyrene and (ii) a divinyl monomer such as $C_4$–$C_{20}$ alkyl and aryl divinyl monomers including divinylbenzene and divinylbutadiene, as has been previously described (Bonn, et al.). One such preferred stationary support is a $C_{18}$-alkylated polystyrene-divinylbenzene copolymer support. The preparation of alkylated polystyrene-divinylbenzene particles for use as a solid support material in accordance with the present invention is described in Example 1.

Briefly, alkylated polystyrene-divinylbenzene particles were prepared by first polymerizing styrene, followed by activated swelling to enlarge the polystyrene beads and increase the degree of crosslinking. Activated swelling was carried out by first mixing the polystyrene beads with 1-chlorododecane, followed by further growing of the resulting swollen beads by addition of ethyldivinylbenzene and divinylbenzene in the presence of an initiator.

The base material composing the solid support is typically alkylated. Alkylation of the base material prevents secondary interactions and can improve the loading of the stationary phase with the ion-pairing reagent to promote conversion of the solid support into a dynamic anion-exchanger.

Typically, the base material is alkylated to possess alkyl groups containing at least 3 carbon atoms, generally between about 3 and 22 carbon atoms, and preferably contains between about 4 and 18 carbon atoms. The base material is alkylated to contain at least 50% surface alkyl groups, and preferably, at least 90% of the surface base material is covered. The alkylated solid support phase may optionally contain functional groups for surface modification. The presence or absence of such functional groups will be dictated by the nature of the sample to be separated and other relevant operational parameters.

Various types of alkylating reagents may be used to alkylate the polymeric solid support. Alkylation may take place either after formation of the polymeric beads as described in Example 1 or before (e.g., by utilizing alkylated monomers to produce alkylated co-polymer beads). Alkylation may be carried out by any of a number of synthetic approaches depending upon the base support material to be alkylated. In an exemplary method for alkylating polymeric base materials containing aryl groups such as polystyrene-divinylbenzene, alkylation is carried out using the Friedel-Crafts reaction, utilizing either tin tetrachloride or aluminum chloride as the Lewis acid catalyst. Alternatively, one may utilize commercially available reverse phase supports containing surface alkyl groups, such as those available from Hamilton (Reno, Nev.) or Hewlett Packard (Wilmington, Del.).

A stationary phase for use in the present method typically has pores with sizes ranging from less than about 30 Å in diameter (e.g., nonporous materials) up to about 1000 Å in size. In using nonporous polymeric support materials, the relatively small pore size excludes many sample compounds from permeating the pore structure and may promote increased interaction with the active surface. The stationary phase may also contain more than one type of pore or pore system, e.g., containing both micropores (less than about 50 Å) and macropores (greater than about 1000 Å).

For achieving separations of samples containing heteroduplexes and homoduplexes of up to about 2000 base pairs in size, the stationary phase will typically have a surface area of about 2–400 $m^2/g$, and preferably about 8–20 $m^2/g$ as determined by nitrogen adsorption.

B. Mobile Phase

The separation method of the present invention utilizes denaturing HPLC, and more specifically, ion-pairing reverse phase HPLC (IP-RP-HPLC). In carrying out the separation according to the present method, the aqueous mobile phase contains an ion-pairing agent and an organic solvent.

The selection of aqueous mobile phase components will vary depending upon the nature of the sample and the degree of separation desired. Any of a number of mobile phase components typically utilized in ion-pairing reverse phase HPLC are suitable for use in the present invention. Several mobile phase parameters (e.g., pH, organic solvent, ion-pairing reagent and counterion, elution gradient) may be varied to achieve optimal separation as will be discussed in regard to the Examples below.

Ion-pairing reagents for use in the invention are those which interact with ionized or ionizable groups in a sample to improve resolution including both cationic and anionic ion-pairing reagents. Cationic ion-pairing agents for use in the invention include lower alkyl primary, secondary and tertiary amines, such as triethylamine (TEA), lower trialkylammonium salts of organic or inorganic acids such as triethylammonium acetate, and lower quaternary ammonium salts such as tetrabutylammonium phosphate. Anionic ion-pairing agents include perfluorinated carboxylic acids.

The hydrophobicity of the ion-pairing agent will vary depending upon the nature of the desired separation. For example, tetrabutylammonium phosphate is considered a strongly hydrophobic cation while triethylamine is a weak hydrophobic cationic ion-pairing reagent. Generally, preferred ion-pairing agents are cationic in nature. One such preferred ion-pairing agent for use in the invention is triethylammonium acetate (TEAA).

The concentration of the ion-pairing agent in the mobile phase is typically between about 0.05 and 1.0 molar, with a preferred concentration of about 0.1 molar. Generally, sample resolution is improved with increasing concentrations of ion-pairing agent. Trialkylammonium salts appear to be useful for obtaining good size-based separation for AT-rich sequences up to about 52° C.

Organic solvents for use in the mobile phase are generally polar solvents such as acetonitrile, methanol, ethanol, ethyl acetate, and 2-propanol. A preferred solvent is acetonitrile.

The pH of the mobile phase will vary depending upon the concentrations of various components. For separation of nucleic acid samples such as RNA or DNA fragments, using temperature to effect at least partial denaturation of the nucleic acid, the pH of the mobile phase is typically maintained between about 7 and 9. Preferably, the mobile phase is maintained at a pH around 7.5.

In an alternate embodiment, the pH of the mobile phase is adjusted to effect at least partial denaturation of the heteroduplex molecules in a sample containing a mixture of homoduplexes and heteroduplexes to allow separation and detection of the heteroduplex molecules. In using chemical means to effect heteroduplex denaturation, the pH may be adjusted by addition of either base (e.g., sodium hydroxide or urea to a pH of around about 8) or acid (e.g., triethylamine and acetic acid at a pH of about 8) under conditions effective to at least partially denature the heteroduplex molecules and which do not degrade the nucleic acids present in the sample nor adversely affect the integrity of the stationary phase. In such cases, sample elution may be carried out at temperatures less than about 50° C.

The concentration of the mobile phase components will vary depending upon the nature of the separation to be carried out. The mobile phase composition may vary from sample and during the course of the sample elution. Gradient systems containing two or more components may be used.

Samples are typically eluted by starting with an aqueous or mostly aqueous mobile phase containing an ion-pairing agent and progressing to a mobile phase containing increasing amounts of an organic solvent. Any of a number of gradient profiles and system components may be used to achieve the denaturing conditions of the present invention. One such exemplary gradient system in accordance with the invention is a linear binary gradient system composed of (i) 0.1 molar triethylammonium acetate and (ii) 25% acetonitrile in a solution of 0.1 molar triethylammonium acetate.

One way to achieve the denaturing HPLC conditions of the present invention (e.g., effective to at least partially denature heteroduplexes) is to modulate column temperature, as will be discussed in reference to the Examples below.

A column temperature typically between about 50°–65° C. is preferred for resolving heteroduplex molecules from their corresponding homoduplex molecules by denaturing HPLC chromatography. The optimal column temperature will depend upon the sequence (base composition) of the sample to be separated, the choice of stationary phase, the choice of mobile phase, pH, flow rate, and the like, and in many cases, will be determined empirically. Ideally, in cases with known sequence, a suitable column temperature may be calculated.

As will be seen from the discussion of the Examples below, heteroduplex detection can, in many cases, be accomplished at a column temperature of about 56° C. Column temperatures as low as about 50° C. can be used for detecting point mutations in small nucleic acid fragments containing up to about 70 base pairs. Column temperatures up to about 63° C. may be optimal for separating G-C rich fragments.

III. HPLC-Promoted Denaturation and Subsequent Detection of Short Oligonucleotide Fragments In addition to providing a denaturing HPLC method for detecting heteroduplex molecules in a sample containing both heteroduplex and homoduplex molecules of essentially the same size, the present method can also be used to detect homoduplex molecules containing short single-stranded overhangs, as illustrated in Example 2. Further, by varying the column temperature, both partial and complete denaturation of a 30-mer homoduplex containing a 2-base overhang was detectable in the resulting chromatograms.

Briefly, two complementary oligonucleotides, oligonucleotide D, a 30-mer, and oligonucleotide E (a 32-mer) were hybridized to form a D-E hybrid with a single stranded two base G-T overhang. The hybrid was then chromatographed on a C18-polystyrene-divinylbenzene support using a binary gradient system composed of 0.1 TEAA (triethylammonium acetate) and 0.1 TEAA containing 25% acetonitrile at two different temperatures, 40° C. and 50° C., respectively. Details of the method including the gradient profile used to elute the sample are provided in Example 2.

Figure 1B:
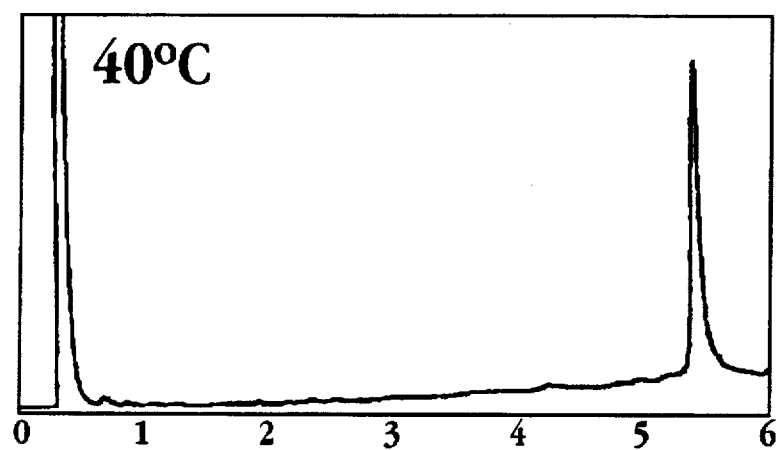
Figure 1C:
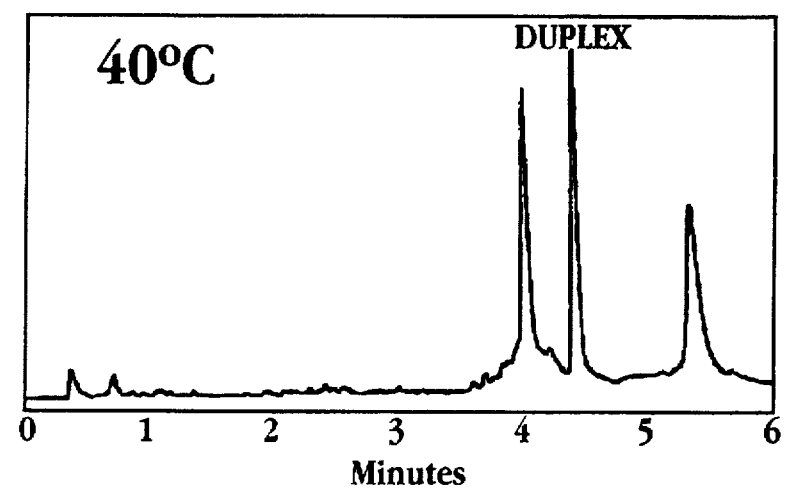

As shown in FIGS. 1A–1C, elution at 40° C. was effective to denature at least a portion of the hybrid molecules in the sample, as indicated by the three peaks seen in FIG. 1C, corresponding to (progressing from shorter to increasing retention times along the horizontal axis) single oligo strand D, the D-E hybrid, and single strand E.

Figure 2A:
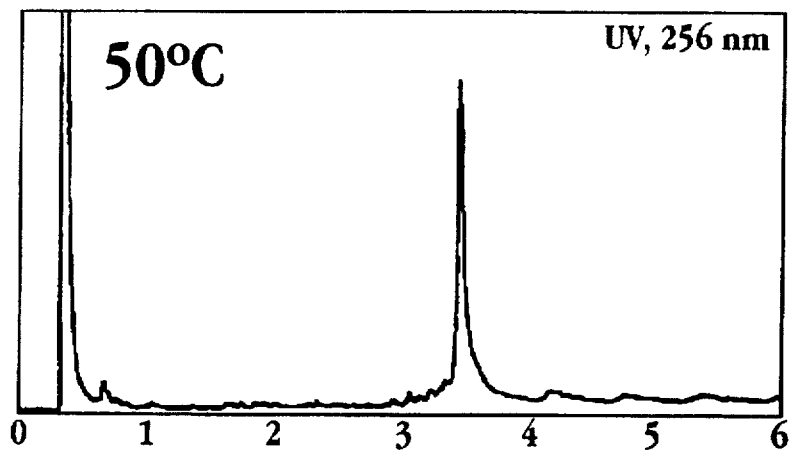
FIGS. 2A-2C show chromatograms resulting from ion-pair reverse-phase (IP-RP) HPLC on a nonporous alkylated poly(styrene-divinylbenzene) solid support maintained at 50° C. for a 30-mer oligonucleotide (FIG. 2A), a complementary 32-mer oligonucleotide (FIG. 2B), and a fully denatured equimolar mixture of the 30-mer and 32-mer (FIG. 2C)
Figure 2B:
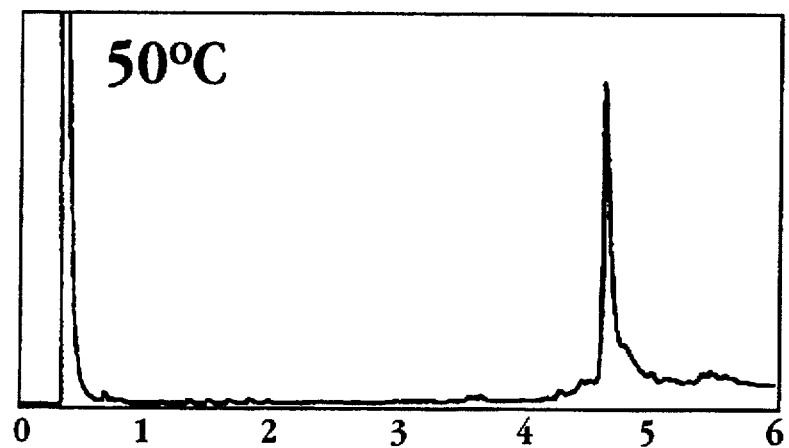
Figure 2C:
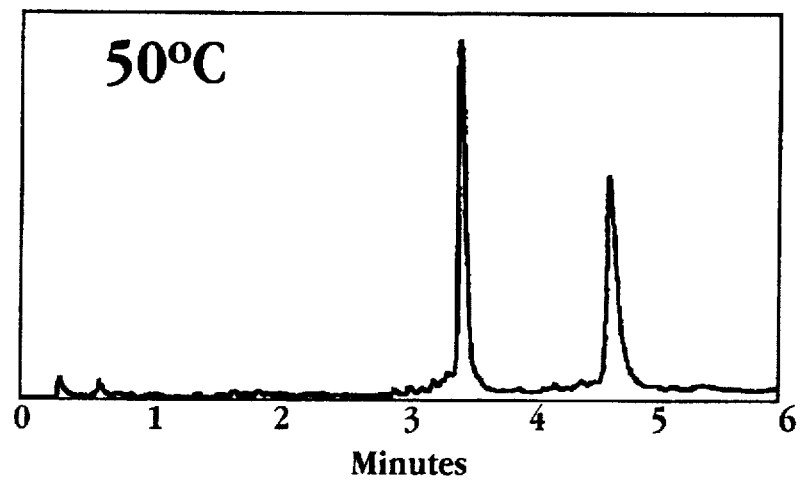

In contrast, elution at 50° C. was effective to denature all of the D-E hybrid molecules in sample, as seen in FIG. 2C. The two peaks in the resulting chromatogram correspond to single stranded oligonucleotides D and E, respectively. The above exemplary results demonstrate that under the denaturing HPLC conditions of the present invention, complementary hybrid molecules containing short overhangs can be denatured and that the extent (e.g., percentage of molecules denatured) of denaturation is a function of temperature. Utilizing the denaturing conditions of the present invention, short homoduplex fragments (i.e., less than about 70 base pairs in length) carrying short overhangs may be detected due to their denaturation during sample elution and detected in the resulting chromatograms as their corresponding single-stranded components.

In initial experiments to test the general applicability of the method, a short heteroduplex 43-mer containing a single base mismatch and lacking an overhang was eluted using the denaturing conditions of the present invention to investigate whether or not such conditions would be effective in denaturing the heteroduplex. The details of the experiment are described in Example 3.

Briefly, liquid hybridization of two 43-mers, oligonucleotide C and oligonucleotide A, a 43-mer complementary, with the exception of one base located ten bases from the 5' end of oligo A, to oligonucleotide C, was carried out by heating an equimolar mixture of the two subject oligonucleotides. The resulting A-C heteroduplex containing a single base pair mismatch was then chromatographed on a C18-polystyrene-divinylbenzene support using a binary gradient system composed of 0.1 TEAA (triethylammonium acetate) and 0.1 TEAA containing 25% acetonitrile at two different temperatures, 40° C. and 51° C., respectively. Details of the method including the gradient profile used to elute the sample are provided in Example 3.

Figure 3A:
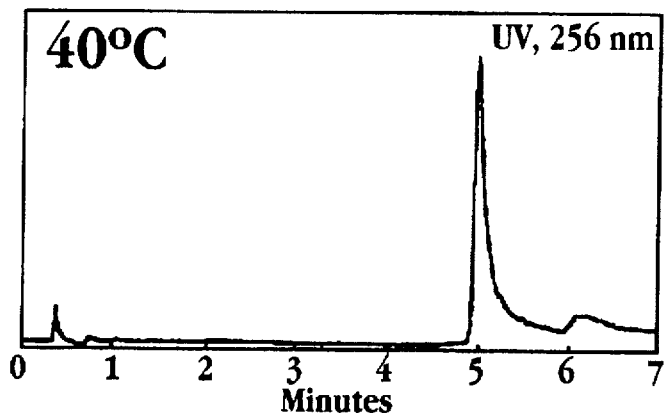
FIGS. 3A-3C are IP-RP HPLC chromatograms of a 43-mer oligonucleotide designated as Oligo A (FIG. 3A, top plot), a 43-mer designated as Oligo C that is complementary with the exception of a single base mismatch to Oligo A (middle plot, FIG. 3B), and an equimolar mixture of the two oligonucleotides (FIG. 3C), at a column temperature of 40° C.
Figure 3B:
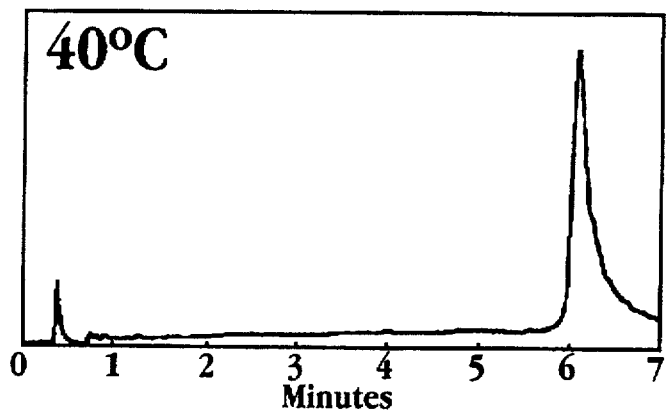
Figure 3C:
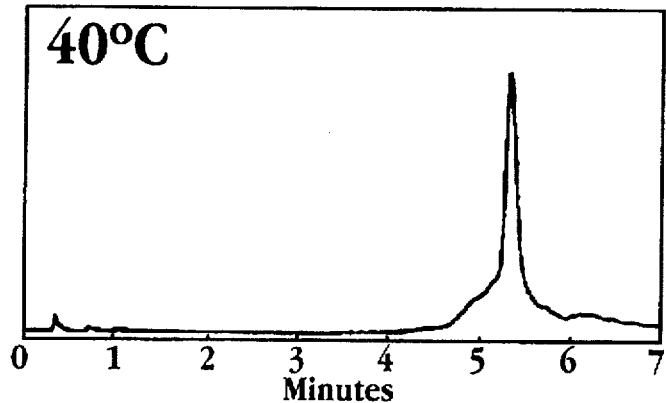
Figure 4A:
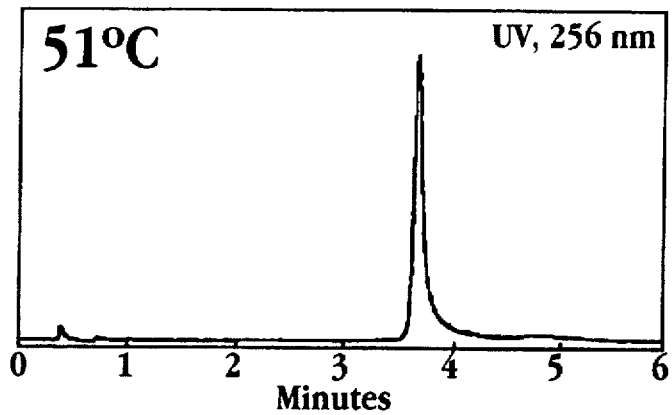
FIGS. 4A-4C are chromatograms of samples identical to those described for FIGS. 3A-3C above, with the exception that the column temperature was maintained at 51° C.
Figure 4B:
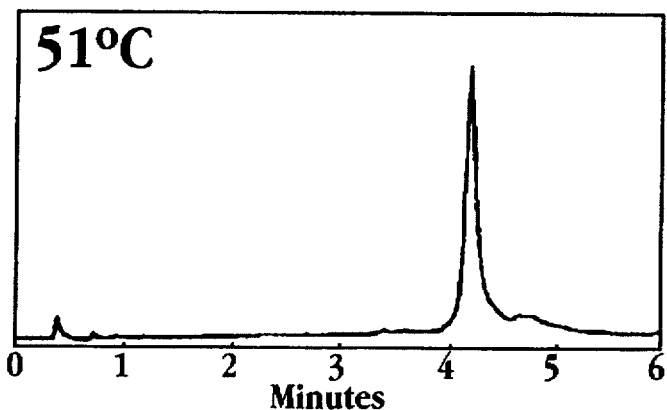
Figure 4C:
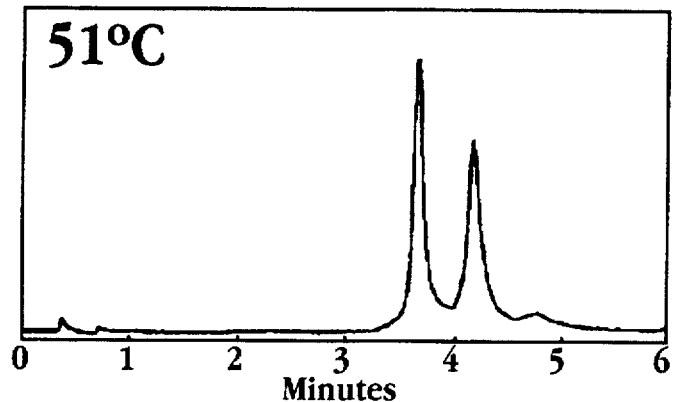

The results of the above described chromatography are shown in FIGS. 3A–C and 4A–C. In contrast to the results described above for the 30-mer homoduplex with a 2-base overhang, at the lower operating temperature of 40° C. (FIGS. 3A–C), elution of the A-C hybrid resulted in a chromatogram corresponding to the annealed oligonucleotide fragments (heteroduplex A-C), as indicated in the resulting chromatogram by a single peak with a retention time differing from that of either oligo A or C. Upon raising the column temperature to 51° C., complete denaturation of the sample was observed, as indicated in FIGS. 4A–C by the detection of two single peaks with retention times corresponding to those of single stranded oligonucleotide A and single stranded oligonucleotide C, respectively. In the exemplary chromatography described above, the effect of increasing column temperature on denaturation and subsequent detection of a heteroduplex molecule under a given set of chromatographic conditions is shown. The above results also demonstrate the ability of the method to discriminate small heteroduplex molecules in a sample by denaturing HPLC and indicate a beneficial feature of the method, namely, to separate oligonucleotides not only as a function of their size but also as a function of their respective sequence.

IV. HPLC-Promoted Partial Denaturation and Detection of Large Heteroduplexes In further support of the method of the present invention, experiments have been carried out in which single base mismatches in heteroduplexes to 1.5 kilobase in size have been detected, as will be described below. Further, a single set of chromatographic conditions was effective for detecting single base mismatches in mixtures of homoduplex and heteroduplex molecules from about 200–1500 base pairs in size, demonstrating the general applicability of the method.

Figure 5:
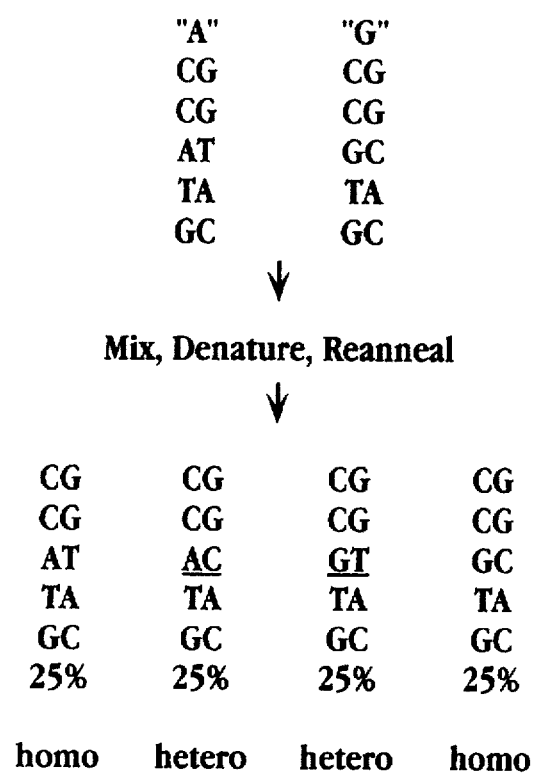
FIG. 5 is a scheme illustrating the mixing of two different double-stranded DNA fragments, subsequent denaturing, and reannealing to produce both homoduplex (2 species) and heteroduplex (2 species) products.

In an exemplary method for detecting polymorphisms in nucleic acid fragments, experiments were carried out in which two different homoduplex molecules, identical in sequence with the exception of one base pair, were denatured and reannealed to form a mixture containing four resulting duplex products, two homoduplexes and two heteroduplexes. Experiments were carried out with pairs of homoduplexes as described above containing 209, 439, 1000, and 1500 base pairs, respectively. Details of the experiments are described in corresponding Examples 4, 5, and 6A,B. A generalized scheme illustrating the mixture of products formed by denaturing and reannealing two such homoduplexes is provided in FIG. 5.

The exemplary polynucleotides used in the set of experiments described below were generally prepared as follows and as described in Example 4. The desired polynucleotide fragments were derived by cloning the representative allelic states of the human Y chromosome STS, sY81 (locus DYS271). STS sY81 displays a single point mutation, an A to G transition, at nucleotide position 168 within the 209 bp STS (Seielstad, et al.). Initially, both the 209 bp "wild type" A allele and the African G allele forms were amplified from human genomic DNA using "touchdown" PCR techniques (Don, et al.) and cloned into the "PCR-SCRIPT SK" (+) cloning vector (Stratagene, La Jolla, Calif.) at the SrfI 728 multiple cloning site using standard molecular techniques. The allelic state of each clonal insert sequence was confirmed by conventional DNA sequencing methods.

Additional clonal types of all possible nucleotide substitutions at the polymorphic position, including 1, 2, 3, and 4 base pair insertion length variants were constructed using oligonucleotide cassette site-specific mutagenesis techniques. Briefly, short synthetic double stranded oligonucleotide inserts containing the desired nucleotide composition were subcloned into the unique Hpa I and Bgl II restriction sites which flank the polymorphic site. Each of the clonal allelic states was confirmed by conventional DNA sequencing. These clones provided precisely defined reagents for subsequent heteroduplex formation and detection. Desired polynucleotide fragments of variable length up to 1500 base pairs, each containing a single known polymorphic nucleotide, were generated by amplifying fragments from the appropriate plasmid clone using sets of PCR primers complementary to the vector sequence which flank the polymorphic locus at various defined distances.

Briefly, as described in Example 4 for experiments performed with 209-mer duplexes, two double stranded polynucleotide PCR products, homo-A-209 and homo-G-209 were subjected to denaturation and reannealing.

Double-stranded DNA homoduplex A, "homo-A-209", a 209-base pair fragment, was composed of two complementary 209-base fragments, polynucleotides 1 and 2. Double stranded DNA homoduplex G, "homo-G-209", a second 209-base pair fragment, was identical in sequence to homo-A-209 with the exception of one base pair (a G-C substituted for A-T present in homo-A-209) and was composed of polynucleotides 3 and 4. Polynucleotide 3 was identical in sequence to polynucleotide 1, with the exception of a guanosine at position 168 from the 5' end of polynucleotide 3, in comparison to an adenosine at the analogous position in polynucleotide 1. In a similar fashion, polynucleotide 4 was identical in sequence to polynucleotide 2, with the exception of a cytosine at position 42 from the 5' end replacing a thymidine in the same position in polynucleotide 2.

The resulting mixture of products, containing original homoduplexes homo-A-209 and homo-G-209 and newly formed heteroduplexes hetero-AC-209 and hetero-GT-209 were then analyzed under the denaturing conditions of the present invention using ion pairing reverse phase HPLC. The designation hetero-AC-209 represents the double stranded product formed by annealing polynucleotides 1 and 4, and contains a single base pair A-C mismatch at position 168 relative to oligo 1. The designation hetero-GT-209 represents the double stranded product formed by annealing polynucleotides 2 and 3, and contains a single base pair G-T mismatch at position 168 relative to polynucleotide 3.

Two separate runs were performed at 50° C. and 54° C. to optimize the effect of column temperature on separation of the product mixture components, as shown in FIGS. 6A–6C and FIGS. 7A–7C, respectively. As will be appreciated, using a given stationary support, adjustments in run parameters such as the components of the mobile phase and relative amounts thereof, pH, gradient profile, flow rate, column temperature, and the like, may be useful in selecting the optimal denaturing conditions for carrying out the separation method of the present invention.

Figures 6A, 6B, 6C:
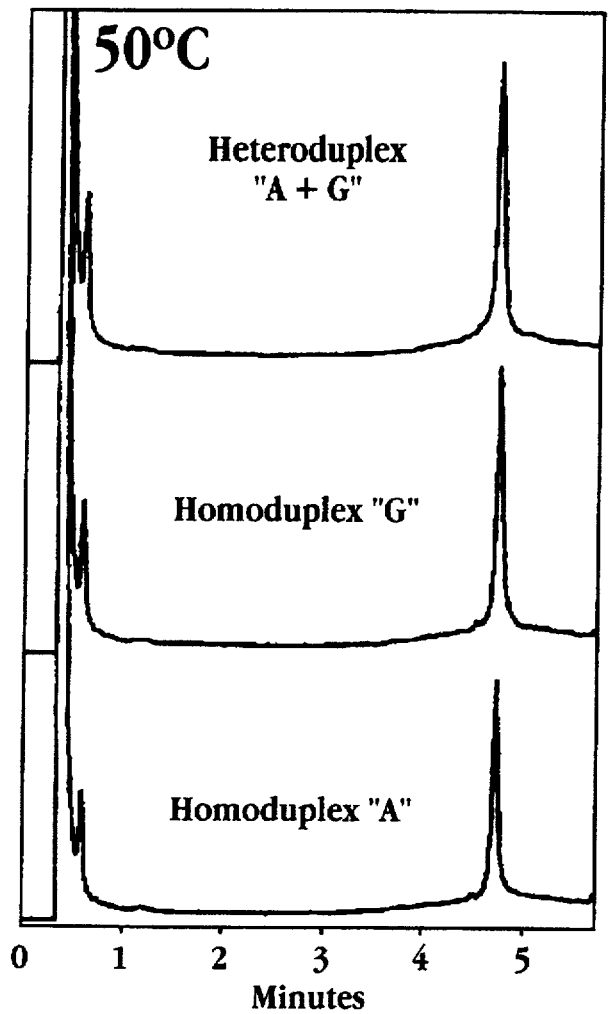
FIGS. 6A-6C are IP-RP-HPLC chromatograms illustrating the detection at 50° C. of a 209-base pair homoduplex "homo-A-209" (FIG. 6A), a 209-base pair homoduplex "homo-G-209" (FIG. 6B), and a chromatogram of the hybrids formed after mixing homoduplexes A and G, denaturing, and reannealing to produce both homoduplex and heteroduplex products (FIG. 6C)

At a less stringent column temperature of 50° C. (FIG. 6C), separation/detection of the individual components of the product mixture containing homo-A-209, homo-G-209, hetero AC-209, and hetero-GT-209 was not achieved (FIG. 6C). As seen in FIG. 6C, the components of the mixture co-eluted as a single peak, with a retention time about equivalent to that of each of homoduplexes homo-A-209 and homo-G-209 (FIGS. 6A,B).

Upon raising the column temperature to 54° C., the resolution of the separation was significantly enhanced as is shown in FIG. 7C. The two same-size homoduplex products were clearly separated both from each other and from the heteroduplexes, which eluted from the column slightly earlier than did the homoduplexes.

Figures 10A, 10B, 10C:
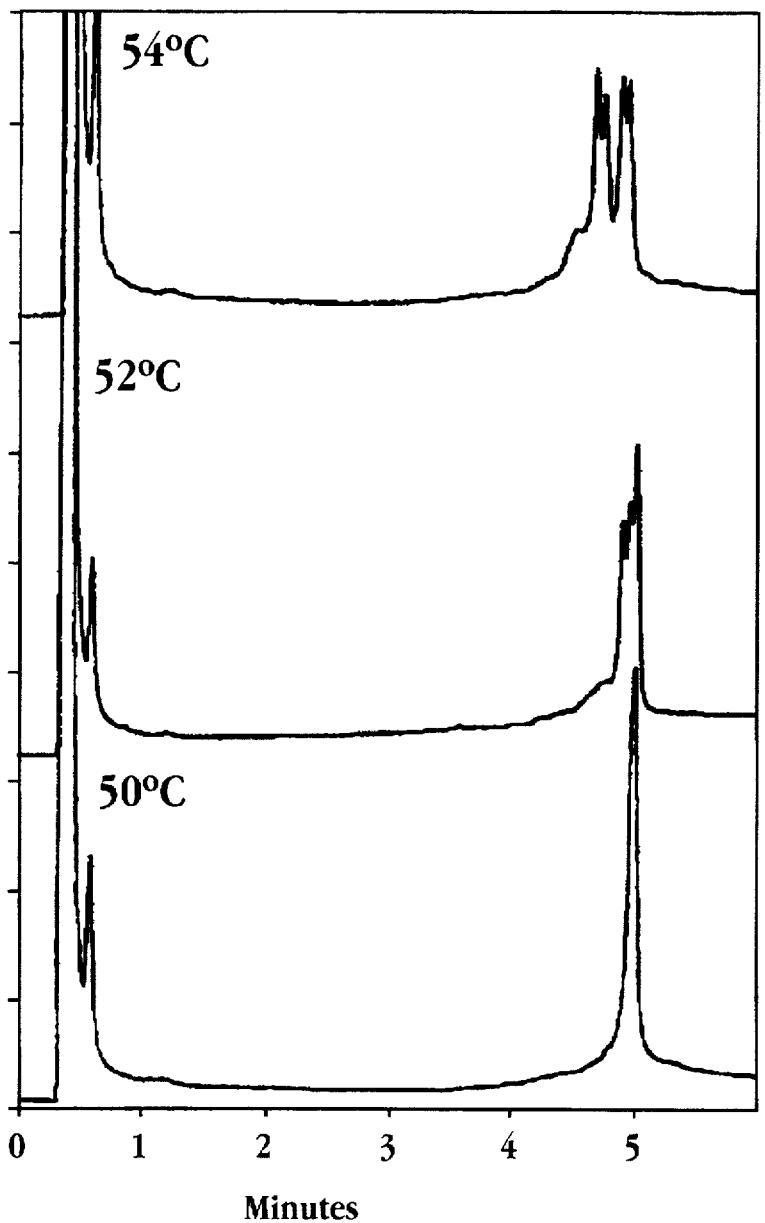

Further to this point, FIGS. 10A–10C illustrate the sensitivity and resolving power of the method as a function of column temperature for samples of homo-A-209 and homo-G-209, subjected to denaturation and reannealing conditions, to produce a mixture containing homo-A-209, homo-G-209, hetero-AC-209, and hetero-GT-209. As seen in FIGS. 10A–C, at 50° C. the mixture elutes as a single peak, with resolution improving at a heightened column temperature of 52° C., and resulting in base line separation of the heteroduplexes from the homoduplex products at an optimized column temperature of 54° C.

In contrast to shorter double stranded DNA fragments having less than about 70 base pairs and containing a single base pair mismatch (e.g., Example 3), based on the number of peaks observed in FIG. 7C, larger DNA fragments appear to be only partially denatured using the optimized denaturing chromatographic conditions of the present invention, resulting in the formation of a "bubble" at the site of the base-pair mismatch. The distortion of the DNA duplex caused by this partial denaturation or bubble appears to cause a shift towards shorter retention times and allows the separation of heteroduplexes containing a single base pair mismatch from homoduplexes of the same size, as illustrated in FIG. 7C.

The results described above show the effective separation of larger nucleic acid duplexes (i.e., over about 70 base pairs) containing a single base pair mismatch from homoduplexes of the same size by partial denaturation of the heteroduplexes using the denaturing HPLC conditions described herein, leading to shorter retention times.

Experiments similar to those described above for the 209-mer duplexes were carried out with 439-mer and 1000-mer duplex molecules at temperatures of both 50° C. and 56° C. The experiments were performed to examine the sensitivity of the method to both temperature and duplex size, as described in Examples 5 and 6A. A similar experiment was carried out with 1500-mer duplex molecules at a temperature of 57° C. and a pH of 7.5, as described in Example 6B and illustrated in FIGS. 12A–12C.

Summarizing the results, at a column temperature of 50° C., each of the mixtures of homo- and heteroduplex products co-eluted and were detected as a single peak. At the lower column temperature, separation of the components of each of the reaction mixtures was not achieved, indicating the sensitivity of the separation method to temperature under the conditions employed.

Figures 8A, 8B, 8C:
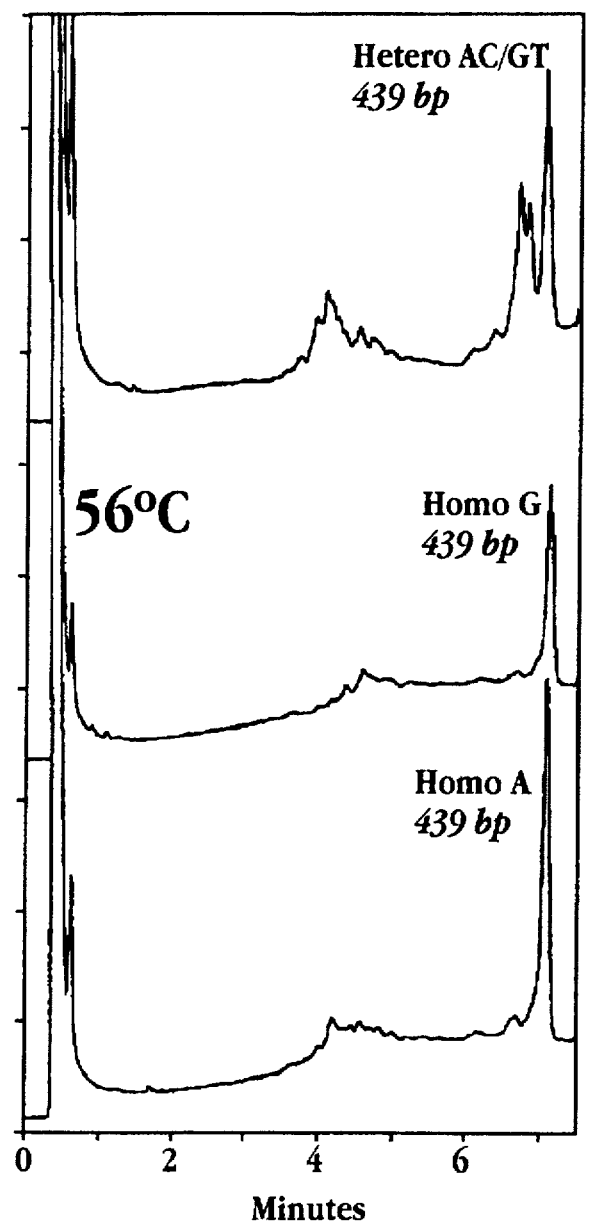
FIGS. 8A-8C are IP-RP-HPLC chromatograms illustrating the detection (at 56° C.) of two 439 base pair heteroduplexes each containing a single site mismatch in a sample containing both 439-mer homoduplex and heteroduplex samples (FIG. 8C).
Figures 9A, 9B, 9C:
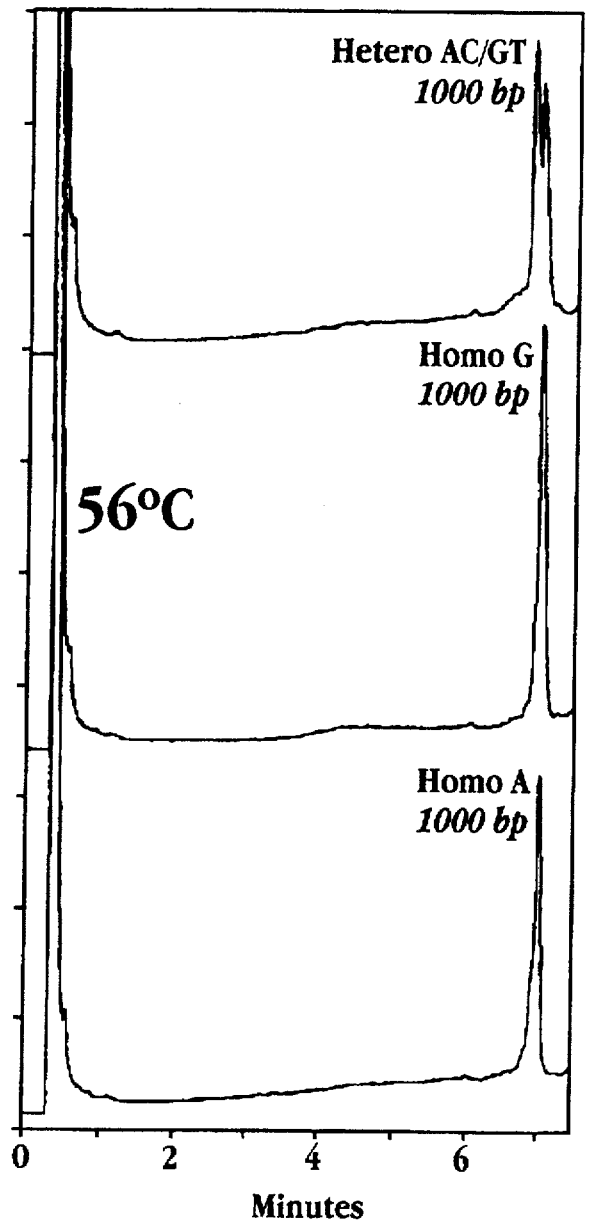
FIG. 9A-9C are IP-RP-HPLC chromatograms of each of two PCR-amplified 1-kilobase homoduplexes, "homo-A-1kb" (FIG. 9A) and "homo-G-1kb" (FIG. 9B).
Figure 12A:
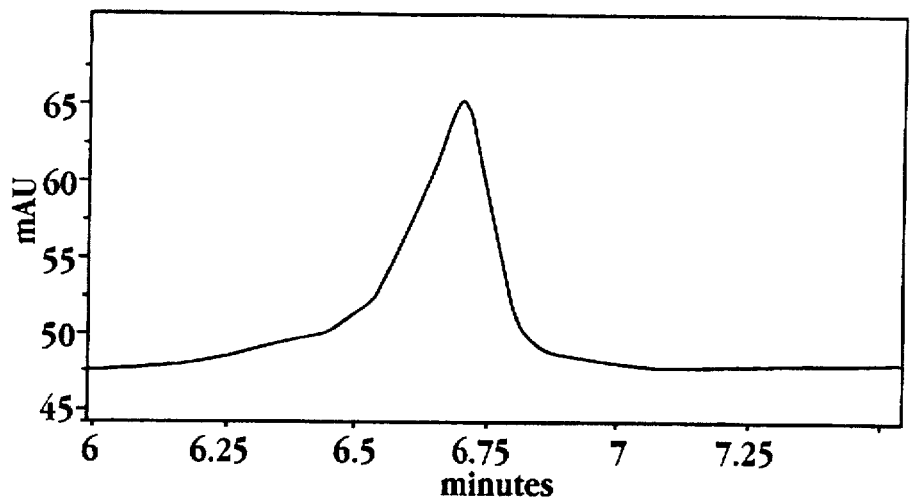
FIGS. 12A-C are IP-RP-HPLC chromatograms of each of two PCR-amplified 1.5-kilobase homoduplexes (FIGS. 12A and 12B) and the detection, at pH 7.5, of two 1.5-kilobase heteroduplexes, each containing a single base-pair mismatch (FIG. 12C)
Figure 12B:
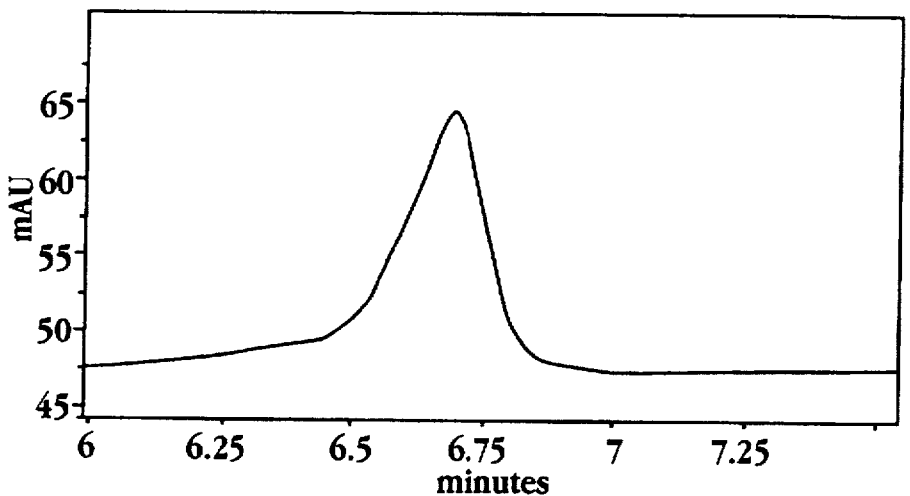
Figure 12C:
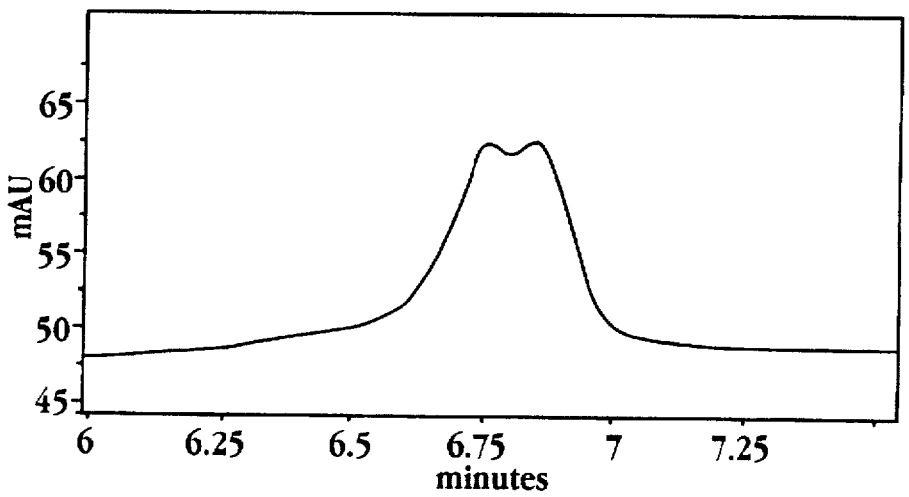

From the chromatograms shown in FIGS. 8C and 9C (column temperature of 56° C.), it can be seen that the present method can be used for detecting single base pair mismatches in heteroduplexes up to at least 1 kilobase in size under chromatographic conditions similar to those used in the separation of shorter nucleic acid fragments, suggesting the general applicability of the method. Using the methods described herein, a single base pair mismatch was detected in polynucleotides 1500 base pairs in length, as illustrated in FIGS. 12A–12C. The results further suggest the potential for detecting single base pair mismatches in duplexes up to 2 kilobase in size.

V. Applications

The method of the present invention can be used to detect heteroduplex molecules obtained by reverse transcription prior to amplification by PCR. The method of the present invention can also be extended to the quantification of competitive reverse transcriptase PCR (RT PCR) reactions, namely via the detection of heteroduplex formation. In competitive RT-PCR, heteroduplex formation is one potential consequence of the homology between competitor and native products. The identification of heteroduplex RT-PCR products can be an important factor in determining the quantitative accuracy of the competitive assay results.

Generally, in competitive RT-PCR, an RNA homolog (competitor) which contains the same sequence which is recognized by the reaction primers for the RNA of interest (native) is modified either by changing the presence of a restriction site or by altering the length of the sequence intervening between the primer binding sites to provide competitor mutant RNA. A range of known quantities of competitor RNA is added to multiple reactions each containing uniform amounts of the RNA preparation to be quantified (native). DNA expression is estimated by observing the relative amount of native and competitor products resulting from RT-PCR (Ferre, et al.; Volkenandt, et al.). The production of heteroduplexes during RT-PCR amplification can be confirmed using the denaturing HPLC method of the present invention.

In using denaturing HPLC to quantify the results of RT-PCR, reverse transcriptase PCR is carried out and the resulting amplification products are typically resolved by agarose slab gel electrophoresis. In order to calculate the amount of native RNA present in the sample, quantification of the amounts of competitor and native products is necessary.

To improve the accuracy in the quantification step, the PCR products resolved by gel electrophoresis may be analyzed using the denaturing HPLC method of the present invention as has been previously described.

In utilizing such an approach, the presence of a peak(s) in the resulting chromatogram that does not correspond to a product observed by gel electrophoresis may correspond to a heteroduplex.

To confirm whether or not a peak detected by denaturing HPLC corresponds to a heteroduplex, native and competitor RNA are reverse transcribed and amplified in separate reactions. The amplification products are then mixed together, followed by IP-RP-HPLC analysis of this mixture. The mixture is then heated (e.g., at 97° C. for 3 minutes) followed by cooling to (e.g., to 4° C.), followed by a second IP-RP-HPLC analysis. The appearance of a new product peak, and comparison of the retention times of any new peaks to those of any unaccounted peaks observed in the chromatograms of the initial set of RT-PCR reactions, indicates heteroduplex formation.

In addition to identifying single base pair mismatches, the HPLC method of the invention can also be used for detecting indels in nucleic acid fragments. In exemplary experiments similar to those described above, a 440-mer homoduplex was mixed with a 439-mer homoduplex, identical to the 440-mer, with the exception of a single base pair deletion. Following denaturation and reannealing, the resulting mixture, containing both the original homoduplex molecules and the newly formed heteroduplexes, was chromatographed by the denaturing HPLC method of the invention (pH 7.0, 55.5° C., 0.1M TEAA/0.1M TEAA in 25% acetonitrile) and heteroduplex formation was observed. The heteroduplex indel molecules were separated from the homoduplex starting reagents in the resulting chromatogram and exhibited shorter retention times than those of the corresponding 439-mer and 440-mer homoduplexes. Using the present method, similar results have been obtained for indels having two, three, and four base pair deletions.

The present method has also been extended to the detection of polymorphic sites contained within HCV (hepatitis C virus). HCV RNA was reverse-transcribed and nested PCR amplification was carried out on HCV variants from human subjects. Single-site polymorphisms were identified by this method.

The method of the present invention may also be enhanced in the case of the analysis of GC-rich sequences for polymorphisms by the utilization of nucleotide analogs, such as deoxyinosine or 7-deazaguanine, during PCR amplification.

VI. Factors Which May Influence Product Resolution

In carrying out the separation method of the present invention, a variety of factors may influence product resolution. While it is not possible to determine an ideal set of conditions suitable for analyzing all possible nucleic acid fragments by the present HPLC method, based upon experiments performed to date, conditions determined to be preferred or found to affect sample resolution are discussed below.

In carrying out the IP-RP-HPLC method of the invention, the nucleic acid sample to be analyzed is typically injected and pre-mixed with the mobile phase prior to elution on the solid support. The sample is then contacted directly with the stationary phase, or alternatively, is passed through a "preconditioning" tubing or pre-column to allow the sample and mobile phase to equilibrate before contact with the solid support.

In one embodiment, the mobile phase components are introduced into a mixer inside the column oven and mixed prior to contact with the sample. Alternatively, the mobile phase components may be mixed at ambient temperature and contacted with the sample injector, also maintained at ambient temperature outside of the column oven. Both of the above variations have been shown to be suitable for detection of heteroduplexes as has been described.

In a preferred embodiment, the sample is injected into the mobile phase, pre-equilibrated to the temperature of the column. In this manner, a near-direct connection between the column and the injector is provided to minimize diffusion and enhance sample resolution.

Alternately, when utilizing a low-pressure HPLC system, sample mixing typically occurs at ambient temperature. In instances in which the autosampler does not provide for heating the injection port to column temperature, standard HPLC tubing (e.g., 0.005–0.01 " diameter) may be positioned between the injector and the column, to heat the mobile phase and induce partial denaturation of the DNA sample. The tubing is preferably fitted with non-DNA binding hardware such as that made of PEEK (polyether ether ketone) or titanium. The length of the tubing is typically determined based upon the efficiency of heat transfer. The entire length of the pre-column may be maintained at oven temperature, or, only a portion of the pre-column may be heated. The sample is passed through the pre-column and then contacted with the stationary phase for subsequent elution.

In investigating the effect of column length and pre-column equilibration on the detection of 1000-mer heteroduplexes, heteroduplex formation was detected using a 60 cm length of tubing between the injector and the column, with a total length of 50 cm maintained at a column temperature of 56° C. Upon increasing the length of tubing to 100 cm (with a total length of 90 cm maintained at an oven temperature of 56° C.), improved separation of the heteroduplex species was observed.

As has been discussed in section IIB above, one parameter which impacts the denaturing HPLC method of the present invention is pH. Generally, the pH of the mobile phase is maintained between about 7 and 9. In attempting to observe a single base mismatch in polynucleotides 1.5 kb in length, a preferred pH for carrying out the separation was found to be 7.5, as is described in Example 6B and further illustrated in FIGS. 12A–12C, and particularly in FIG. 12 C, which indicates heteroduplex detection in polynucleotide molecules containing up to 1500 base pairs.

Another factor which affects the parameters to be selected for carrying out the separation method of the invention is the composition of the sample sequence to be analyzed. In this respect, for samples containing a polymorphic site flanked by a GC-rich region, higher temperatures may be required to detect the polymorphism.

In investigating the effect of sample sequence on the temperatures effective for heteroduplex separation, the denaturing HPLC method of the invention was used to detect polymorphic sites contained within the 31-A-G fragment of the β-globin gene (Myers, et al., 1986), where the region containing the polymorphism is flanked by GC-rich segments.

Briefly, the experiment was carried out essentially as described in Example 4, using amplified nucleic acid segments with polymorphic site flanking regions that are GC-rich. DNA was obtained from plasmids carrying mutant mouse β-major globin promoter-31 A-G, having a single base A-to-G substitution at position 31 in the promoter, relative to the start site of transcription, and amplified using sequence specific forward (SEQ ID NO:11) and reverse (SEQ ID NO:12) primers.

Figure 13A:
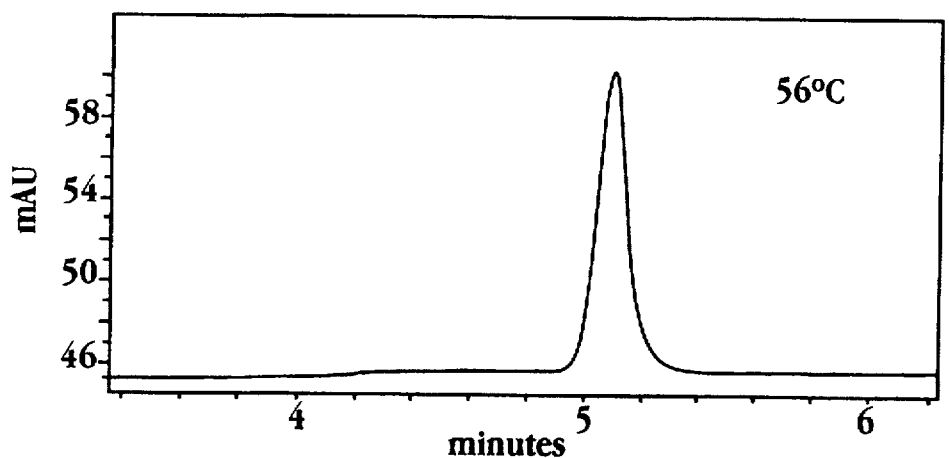
FIGS. 13A-13E are IP-RP-HPLC chromatograms of a segment of the β-globin gene containing a polymorphic site flanked by a GC-rich region, illustrating the effect of temperature on sample resolution for detecting heteroduplexes.
Figure 13B:
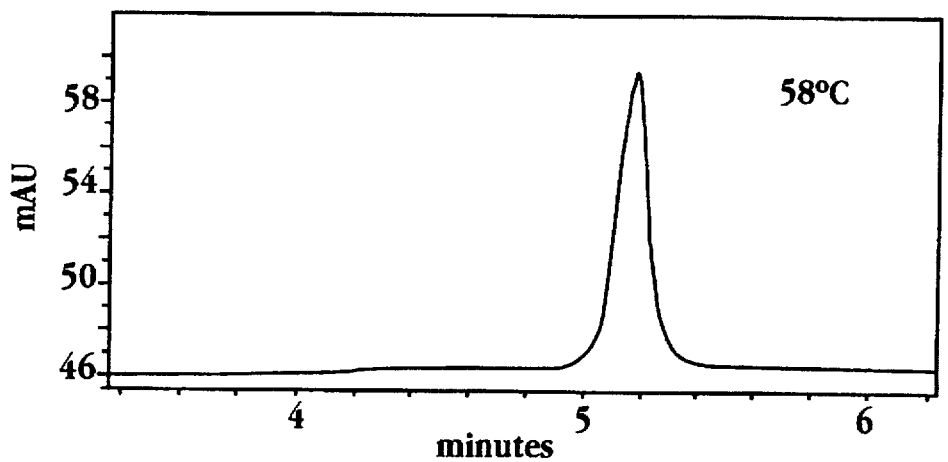
Figure 13C:
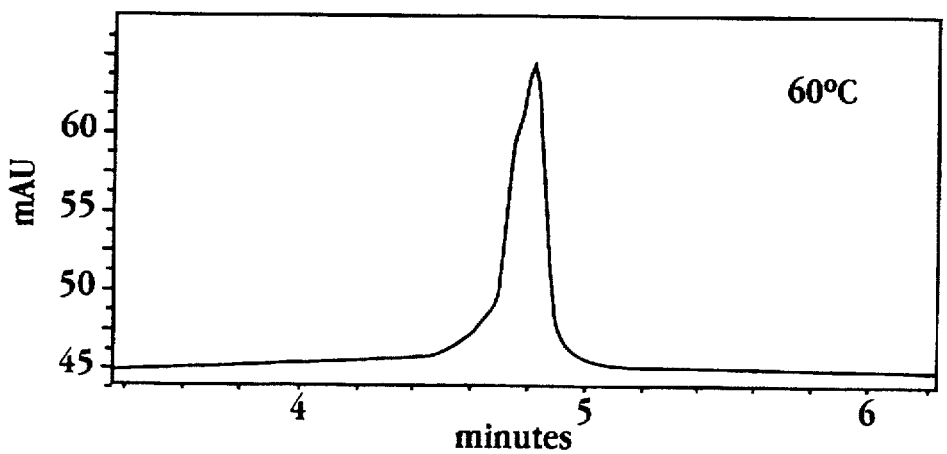
Figure 13D:
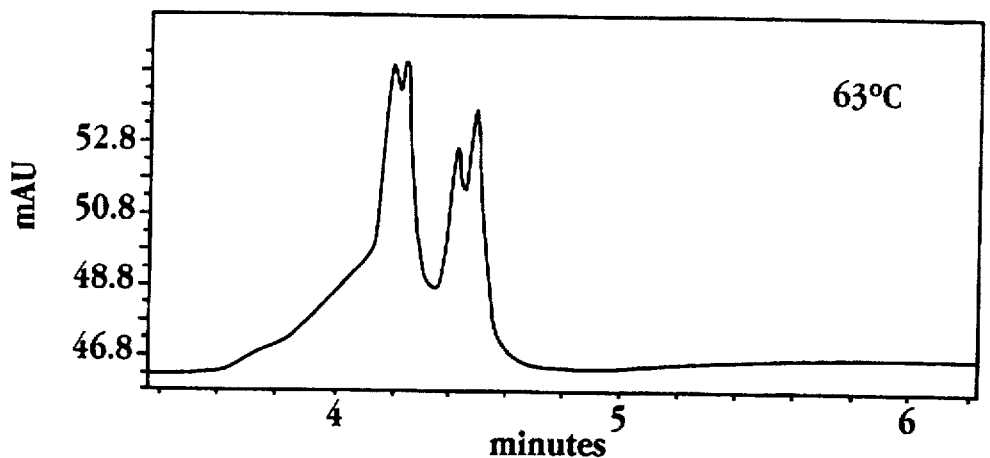
Figure 13E:
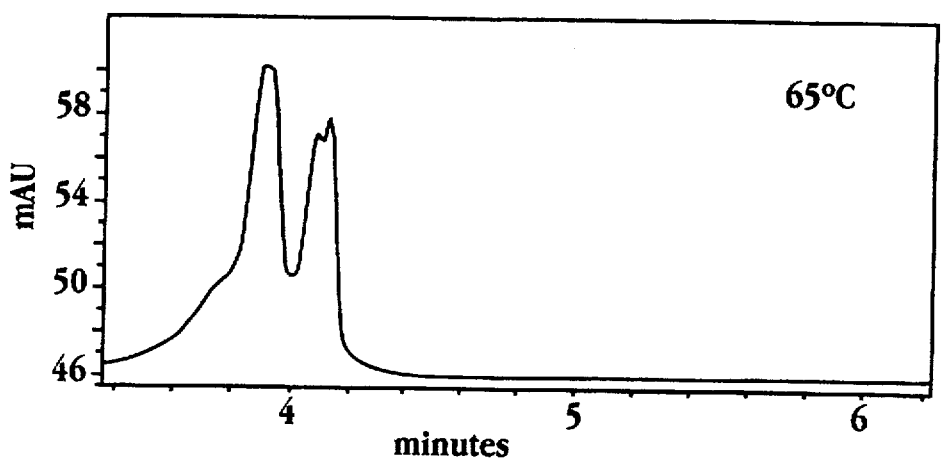

The results are illustrated in FIGS. 13A–13D. The sample containing a mixture of duplexes (both hetero and homo) was eluted at temperatures of 56° (FIG. 13A), 58° (FIG. 13B), 60° (FIG. 13C), 63° (FIG. 13D), and 65° C. (FIG. 13E), under conditions similar to those which have been previously described. As is apparent from FIGS. 13 A–E, for the above sample, resolution was found to increase with increasing column temperature, up to about 63° C., at which temperature a preferred sample resolution was obtained. However, as the temperature was increased to 65° C., a loss in resolution was observed, reinforcing the sensitivity of the method to a number of variables, including temperature.

The results of the above experiment indicate that although in most cases a temperature of 56° C. is effective for heteroduplex separation, in some instances, and particularly for polynucleotides containing polymorphisms flanked by GC-rich regions, higher temperatures may be necessary.

VII. Polymorphic Site Identification

The present invention provides a general method for screening for polymorphisms and sequence variations between similar nucleic acids isolated from different sources. Exemplary of this screening method, the present method has been used to identify previously unknown polymorphic sites on the human Y chromosome.

The denaturing HPLC method of the present invention was used to screen for polymorphic sites on sections of the human Y chromosome, namely from loci DYS199, DYS198, DYS234, DYS253 and DYS263. DNA fragments from the human Y chromosome obtained from human genomic DNA sources were amplified using allele specific PCR as described in Example 8. Polymorphic site identification was confirmed by subsequent conventional sequencing techniques.

For each of the loci examined, control amplification products were separately mixed with amplification products from samples of different geographical origins (e.g., Africa, Asia, Oceania, Europe, Americas). Each set of mixed, amplified fragments were heat denatured and allowed to reanneal and the resulting sample mixtures were then analyzed by denaturing HPLC in accordance with the present invention.

Figure 11A:
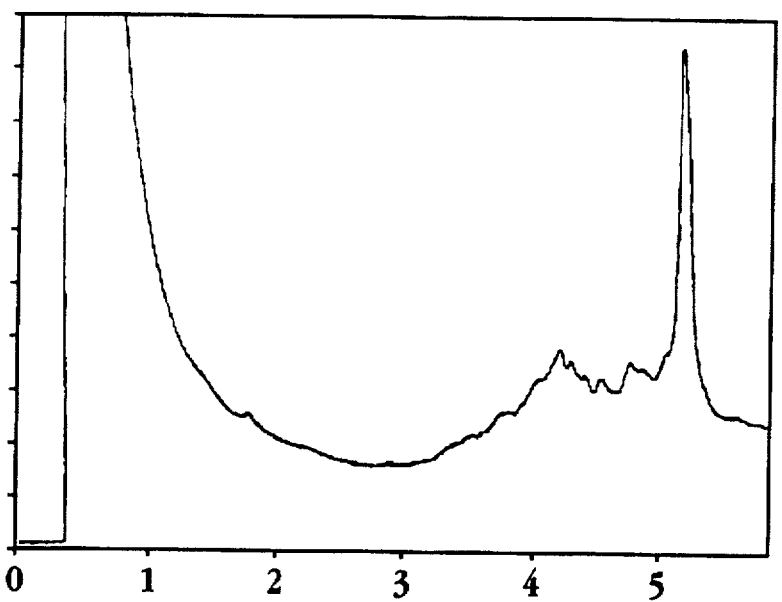
FIG. 11A-11B are IP-RP-HPLC chromatograms of separations carried out at 56° C. illustrating the detection of a polymorphic site on the human Y chromosome occurring in native South Americans (FIG. 11B) in comparison to a control group (FIG. 11A)
Figure 11B:
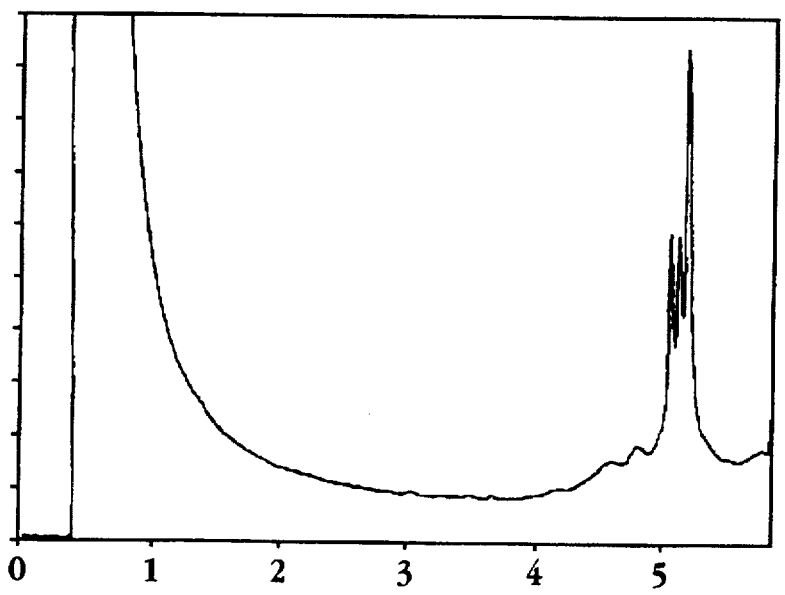

Exemplary chromatograms of DYS199 samples are shown in FIGS. 11A and 11B, illustrating HPLC traces of (i) a sample containing only homoduplex molecules derived from samples of African and Italian origin (FIG. 11A), and (ii) samples of African and native South American origin, indicating the presence of heteroduplexes. Of the samples examined, only samples of native South American origin exhibited the detected polymorphism.

The nature of the base pair mismatch was then verified by DNA sequencing. In greater than 90% of the samples of native South American origin, a single polymorphic nucleotide substitution, a C-to-T transition, was observed at base position 181 of locus DYS199.

As mentioned above, using the present method, polymorphic sites have also been identified at the following Y-chromosomal loci: DYS198, DYS234, DYS253 and DYS263, as summarized in Table 3.

VIII. Utility

The denaturing HPLC method of the present invention has potential applications in a wide variety of areas, including linkage analysis, evolutionary studies, forensics, identification of disease-causing gene mutations, genetic marker development, and the like. The method of the present invention requires only small amounts (typically less than about 100 nanograms) of unpurified sample, yields results in minutes, utilizes on-line detection, and is adaptable to complete automation.

The heteroduplex separation and detection method of the present invention based on heteroduplex formation (e.g., of PCR products) is faster, simpler, more sensitive and more informative than the currently available procedures (such as RNase A cleavage mismatch). The denaturing HPLC method of the invention detects heteroduplex molecules in a mixture containing both heteroduplexes and homoduplexes by utilizing conditions effective to at least partially denature the heteroduplexes. Under such denaturing conditions, heteroduplexes exhibit slightly different retention times (typically shorter) from their homoduplex counterparts, thus providing a sensitive and convenient assay for detecting heteroduplex formation.

Using the conditions described above, base pair mismatches and indels can be observed in heteroduplexes using the method of the present invention. The preferred size range for these heteroduplexes ranges from approximately 30 to 1000 base pairs in length, although larger-sized heteroduplexes can be used as well. Heteroduplexes formed from molecules with mismatched nucleotides were detected in duplexes having a degree of divergence was as low as about 0.1%, and even lower. In addition, more complex mixtures of restriction fragments (e.g., 100–1000 bp size range) resulting from the post-PCR digestion of longer amplification products can be surveyed for the presence of heteroduplexes.

Experiments performed in support of the present invention have led to the development of a comparative nucleic acid sequencing assay which rapidly assesses DNA sequence variation without large scale conventional DNA sequencing approaches and which allows tracking and quantitation of variant genotypes in mixtures of such variants. Further, the method of the present invention allows such estimates with greater accuracy than anything but very large scale redundant DNA sequencing would allow.

In one aspect, the denaturing HPLC method of the present invention is used to detect polymorphisms in physically mapped DNA fragments to thereby provide large numbers of low mutating genetic markers for use in gene mapping. Such markers provide landmarks used to characterize regions in the human genome.

Since the majority of human variation is due to polymorphisms derived from simple nucleotide substitutions and insertions or deletions, a method which provides a means for rapid identification of single site variations among long fragments of DNA can be of tremendous use. Such a method can be utilized to provide a category of genetic markers exhibiting both i) a high density of occurrence and ii) an extremely low mutation rate, making such markers more attractive than existing genetic markers such as microsatellites (Weber, et al.) and minisatellites (Jeffreys, et al.).

In utilizing such an approach, physically mapped fragments (including sequence-tagged sites (STS) and expressed sequence tags (ETS), (Cox, et al.) which contain polymorphisms are used as markers for gene mapping.

The present method facilitates the development of new genetic markers that are both physically and genetically mapped. Polymorphic sites are identified by the present method. Identification of one such site is described in Example 8 where a sequence variation (namely, a single base-pair substitution) was discovered in a segment of the Y chromosome for a population of native South Americans in comparison to samples derived from various other populations. These results are illustrative of using the denaturing HPLC method described herein for the rapid estimation of the degree of relatedness between members of gene families.

In utilizing this approach, a collection of polymorphic genetic markers is provided which is more densely and evenly distributed for traditional pedigree based linkage analysis. For example, after identifying polymorphic sites in a given physically mapped DNA fragment (e.g., amplified from various sources), the positions of identified polymorphic sites in the genetic map are assigned, either by standard linkage analysis or alternatively, based upon the physical distance of any such new polymorphisms from other previously genetically mapped markers (e.g., microsatellites).

Further, the method provides large numbers of low mutating markers for mapping genes involved in complex traits such as chronic diseases such as hypertension.

The present invention provides a method for comparative DNA sequencing in which potentially all possible nucleotide mismatches and insertion/deletions within select amplified DNA fragments obtained from multiple animal or human subjects can be detected. In the context of the present invention, comparative DNA sequencing is carried out by amplifying DNA samples, typically up to at least about 1.5 kb in length, obtained from multiple subjects. The amplified DNA fragments are then surveyed, either individually or in pools containing up to about 10 samples, for the presence or absence of heteroduplexes using the denaturing high performance liquid chromatography method of the present invention. In surveying the samples, the amplified DNA fragments are denatured and allowed to reanneal. The resulting mixture of DNA fragments is then applied to a stationary reverse-phase support. The sample mixture is eluted with a mobile phase containing an ion-pairing reagent and an organic solvent. Sample elution is carried out under conditions effective to at least partially denature any heteroduplexes present in the sample and results in the detection of any heteroduplex molecules contained in the sample. The detection of a heteroduplex indicates the presence of a base pair mismatch and/or an insertion/deletion in the sample fragment(s).

In instances in which only homoduplexes are observed during the sample screening, further standard sequencing is not required since the sequence is monomorphic (e.g., lacking polymorphic sites) in all subjects compared. In utilizing the method of the present invention, only those DNA fragments identified as heteroduplexes, and therefore identified as containing at least one polymorphic site, are then sequenced by conventional methods to characterize the observed polymorphism(s).

Using the present denaturing HPLC method, large numbers of comparative DNA samples can be rapidly and efficiently pre-screened for the presence (or absence) of polymorphisms, and only those samples identified in the pre-screening as possessing polymorphic sites need be further characterized, typically by conventional sequencing techniques. Such genomic analysis can be performed using any genomic nucleic acid material, for example, from mammals, fish, reptiles, plants, or other organisms of interest.

The present method can also be used for forensic applications such as DNA fingerprinting. DNA fingerprinting requires the identification of a set of polymorphic loci, selected so that the probability that two individual DNA samples with identical haplotypes could by chance come from different individuals is very low. The method provides an efficient approach for identifying low mutating polymorphic sites along lengths of contiguous sequence such that the probability of recombination is quite low, increasing the likelihood of the preservation of haplotype information desirable for forensic utilization.

In addition to analysis of genome diversity, the method of the present invention can be applied to the analysis of any number of microorganisms including bacteria, parasites, and other infectious agents. Exemplary microorganisms include, but are not limited to, the following:

(i) Bacterial. Haemophilus—outer membrane proteins, Staphylococcus, Chlamydia—outer membrane proteins, Enterococcus, Mycobacterium (*Mycobacterium tuberculosis*);

(ii) Viral. Feline Leukemia Virus (FeLV), Simian Immunodeficiency Virus (SIV), Human Immunodeficiency Virus (HIV), Hepatitis C Virus (HCV); Human papilloma virus (HPV);

(iii) Fungi. Pneumococcus—Choline dependent Pneumococcal murein hydrolases; 18S rDNA sequences for human pathogenic fungi including Trichophyton, Histoplasma, blastomyces, coccidioides, Pneumocystis (*Pneumocystis carinii*) and Candida (*Candida albicans*) (Bowman, et al.);

(iv) Parasites. Onchocerca (Zimmerman, et al.), *Babesia spp.* (Ellis, et al.), *Giardia spp.* (Weiss, et al.), *Leishmania spp.* (Briones, et al.), *Trypanosoma spp.* (Breniere, et al.); and (v) Mycoplasma. Lyme disease, *Mycoplasma pneumoniae* (Kleemola, et al.), using, for example, sequences derived from 16S RNA.

Typically, probes for any target nucleic acid can be selected from a region of the microorganism's genomic material, such as rRNA (for example, as in Weisburg, et al.). In this way probes can be identified that will form homoduplexes to identify specific species. Formation of heteroduplexes indicates that the sequences have diverged from the probe sequence.

The method of the present invention can also be applied to the analysis of any nucleic acid containing entity, including subcellular organelles such as chloroplasts and mitochondria.

Further, the method of the present invention can also be used in screening methods for the evaluation of therapeutic treatments of any of the above microorganisms. The methods disclosed herein are useful for evaluating, in mixtures of nucleic acids (such as, nucleic acids obtained from tissue samples), the effect over time of a disease treatment, on DNA sequence variation of a nucleic acid target sequence associated with the disease. Therapeutic treatments typically are directed to the resolution, elimination, or relief of a disease state, as, for example, caused by a microorganism/ infectious agent.

In one exemplary application, the present method is used to monitor infection and any changes that might occur during treatment. As applied to infection, the denaturing HPLC method of the invention can be used to establish a base-line of infection in any selected patient before the onset of treatment. Typically, blood and plasma samples are then serially collected from the subject throughout the therapeutic trial.

In one exemplary application, the method of the present invention can be used to monitor the effects of a disease treatment, such as in the case of tuberculosis (TB). The denaturing HPLC separation method of the present invention can be used to monitor the presence and diversity of strains of *Mycobacterium tuberculosis* growing within an individual. For example, a 383 bp segment of the gene encoding the 65 kDa mycobacterial surface antigen can be amplified (Ghossein, et al.) from samples obtained from a patient under treatment and analyzed by the method of the present invention.

The present method can also be used to detect the specific loss or increase in abundance of TB variants during therapy.

Generally, the method of the present invention can be used to monitor when variants come and go within the course of any infection and what the impact of any treatment has on the variant populations. Specific loci associated with drug resistance for a particular microorganisms can be used for tracking different populations of a microorganism using the methods of the present invention, where the variant loci are amenable to detection using ion-pairing reverse phase HPLC.

The present assay can be used to evaluate diversity in cell culture systems and animal models as well as patients.

Additionally, phylogenetic relationships can be established by the method of the present invention. Phylogenetic analysis can be carried out with almost any selected genomic sequence, such as, glycolytic enzymes (like phosphoglycerate kinase (Vohra, et al.)) or rRNA sequences. Phytogenic relationships between plants can be established, using, for example, sequences derived from plastid ribosomal RNA operons (Wolfe, et al.).

Another embodiment of the present invention is the use of specific probes to identify variants based on the formation of homoduplex complexes. For example, sequences corresponding to a particular virus variant can be cloned and amplified. These cloned sequences are then used as a probe against viral molecules isolated from a number of test sources. Using the method of the present invention, if homoduplexes are formed in hybridization reactions between the probe and the test source, then the test source is shown to be similar to the cloned probe variant. If on the other hand heteroduplexes are formed between the probe and test sequences, then sequence divergence between the probe and test sequences is indicated.

With respect to cancer, once a diagnosis has been made, and a region of DNA associated with the cancerous growth has been identified, the heteroduplex separation method of the present invention can be used to evaluate the extent of infiltration of tumor cells within a tissue population. Exemplary potential target sequences are protooncogenes, for example, including but not limited to the following: c-myc, c-myb, c-fos, c-kit, ras, and BCR/ABL (e.g., Gazdar, et al.; Wickstrom; Zalewski, et al.; Calabretta, et al., 1992, 1993;), oncogenes/tumor suppressor genes (e.g., p53, Bayever, et al.). In tumor cells, deletions, insertions, rearrangements and divergent sequences in such genes or in the regions of DNA surrounding the coding sequences of such genes, all allow formation of heteroduplexes between amplified variant DNA and amplified DNA from normal cells.

In view of the above discussed applications, it can be seen that the method of the present invention provides the means to determine approximate levels of DNA sequence diversity in a population of nucleic acid sequences both within and between individuals.

Typically, samples to be analyzed by the method of the present invention are obtained by polymerase chain reaction amplification—the amplified sequences are denatured and reannealed before HPLC analysis. In addition to obtaining nucleic acid samples by amplification, other samples sources can be used as well. For example, sequences of interest can be cloned (e.g., in a lambda vector; Sambrook, et al.) from two different sources. The sequences of interest are independently isolated away from vector sequences (e.g., by restriction endonuclease digestion and fragment purification). These two samples can then be combined, denatured, renatured, and the resulting heteroduplexes analyzed in accordance with the present method.

The following examples illustrate, but in no way are intended to limit the scope of the present invention.

General Procedure

A. Oligonucleotides and Polynucleotides

Synthetic oligonucleotides were prepared using commercially available automated oligonucleotide synthesizers. Alternatively, custom designed synthetic oligonucleotides and polynucleotides may be purchased, for example, from Synthetic Genetics (San Diego, Calif.). Large oligonucleotide and polynucleotide sequences can be created by a series of cloning steps involving a tandem array of multiple oligonucleotide fragments corresponding to the sequence of interest (Crea; Yoshio, et al.; Eaton, et al.).

Oligonucleotides and polynucleotides may also be obtained by polymerase chain reaction (PCR). In this case, primers are selected flanking the sequence of interest and amplification of the oligonucleotide/polynucleotide of interest is carried out by standard procedures (Mullis; Mullis, et al.). Source nucleic acid for the oligonucleotides of interest may be RNA (Kawasaki, et al.; Wang, et al.) or DNA.

A "HOT START PCR" can be performed (D'Aquila, et al.), using standard techniques ("AMPLIWAX", Perkin-Elmer Biotechnology, Norwalk, Conn.), in order to make the PCR amplification more robust for amplification of diverse sequences, which ideally require different amplification conditions for maximal sensitivity and specificity.

PCR can also be carried out using reaction conditions that allow for the amplification of long target sequences ("rTth-XL" polymerase and "XL PCR BUFFERS", Applied Biosystems, Foster City, Calif.). The types of systems used for these "long-range" PCR reactions contain a mixture of polymerases one of which has proof-reading activity (i.e., 3' to 5' exonuclease activity) that corrects misincorporated nucleotides, an event that if uncorrected can retard further polymerization, ultimately limiting the size of sequence efficiently amplified. The exclusive use of thermostable polymerases with proof-reading activity in PCR such as Pfu I (Stratagene, La Jolla, Calif.) or ULTma (Perkin Elmer, Norwalk Conn.) yield higher fidelity PCR products and are preferred for cloning and subsequent gene expression studies.

Amplification products can be separated from excess PCR primers by a single pass through a "WIZARD PCR COLUMN" (Promega, Madison, Wis.) following the manufacturer's instructions. The "WIZARD PCR COLUMN" is a silica based resin that binds DNA in high ionic strength buffers and will release DNA in low ionic strength buffers. Alternatively, columns such as Qiagen "QIAQUICK" columns may be used. The amplified DNA is eluted from the column with 50–100 μl distilled water.

B. Reagent Sources

HPLC gradient-grade acetonitrile and standard chemical reagents were typically obtained from Merck (Darmstadt, Germany). Triethylammonium acetate (TEAA), pH 7.0, was obtained from Applied Biosystems (Foster City, Calif.). HPLC-grade triethylamine was obtained from Fisher Scientific (Pittsburgh, Pa.), the pH of which was adjusted (to pHs ranging from about 7–9) by the addition of HPLC reagent grade acetic acid (Fisher Scientific, Pittsburgh, Pa.). High purity water used for preparing buffer solutions was obtained using a Milli-Q water system (Millipore, Milford, Mass.).

C. High Performance Liquid Chromatography

High performance liquid chromatography was performed on a high pressure gradient HPLC system consisting of two high-precision high-pressure gradient pumps (Model S1100, SYKAM, Gilching, Germany), a controller (Model S2000, SYKAM, Gilching, Germany), a column oven (Model S4110, SYKAM), with a stability of ±0.1° C., and a UV detector (Model UVIS 200, LINEAR, Fremont, Calif.). The dynamic high pressure-gradient system was fitted with a 200 μl mixing chamber and sample injection loop installed directly in the column oven.

For experiments describing pre-conditioning, a low pressure gradient system from Gynkotek (Germering, Germany) was used.

D. Equilibration of Newly-Packed Columns

Newly-packed columns containing a polystyrene-divinylbenzene stationary phase were typically equilibrated by first washing the column for at least 2 hours with 0.1M TEAA, at pH 7.0–9.0, in 25% acetonitrile, at a flow rate of 0.5 ml/minute and a temperature of 50° C.

The mobile phase was then adjusted over a 3 minute period to the starting conditions of the linear gradient to be used for sample separation prior to sample injection.

Conditioning times of 1–2 hours were determined to be sufficient for column equilibration, although overnight equilibration was found to be preferable for maximum column performance.

E. Column Regeneration

Following sample separation, the stationary phase was washed with 90%–100% Eluent B (22.5–25% acetonitrile) for 1–2 minutes at the gradient sampling conditions.

The rapid regeneration of the stationary phase allows fast and repetitive injections, thus providing a highly efficient and rapid analytical tool.

EXAMPLE 1

Preparation of Alkylated Nonporous Poly (Styrene-Divinylbenzene) (PS-DVB-$C_{18}$) Particles Sodium chloride (0.236 g) was added to 354 ml of deionized water in a 1.0-liter volume reactor equipped with a mechanical stirrer, reflux condenser and a gas introduction tube. Dissolution of the sodium chloride was carried out under an inert atmosphere of argon, assisted by stirring (350 rpm) at 87° C. To the sodium chloride solution was added freshly distilled styrene (33.7 g) and 0.2184 g potassium peroxodisulfate dissolved ($K_2S_2O_8$) in 50 ml deionized water. Immediately following addition of styrene and potassium peroxodisulfate, the gas introduction tube was pulled out of the solution and positioned above the liquid surface. The resulting reaction mixture was then stirred for 6.5 hours at 87° C. The contents of the reactor were cooled to ambient temperature and diluted to a concentration of 54.6 g of polymerized styrene per a 1000 ml volume of suspension. The quantity of polymerized styrene per liter of suspension was approximated to include the amount of polymer adhered to the mechanical stirrer (from 5–10 g). The diameter of the resulting spherical beads in suspension was determined to be about 1.0 micron by light microscopy.

The resulting beads were generally too small and too soft (e.g., having low pressure stability) for use as chromatographic packings. In order to improve the pressure stability of the beads, the beads were enlarged and the degree of crosslinking was increased in a second processing step, based on the activated swelling method described by Ugelstad, et al.

To initiate activated swelling, the aqueous suspension of polystyrene seeds (200 ml) was mixed first with 60 ml acetone followed by 60 ml of a 1-chlorododecane emulsion. The 1-chlorododecane emulsion was prepared by forming a mixture of 0.206 g sodium dodecylsulfate, 49.5 ml deionized water and 10.5 ml 1-chlorododecane. The resulting mixture was maintained at 0° C. and sonicated for 4 hours until a fine emulsion of <0.3 microns was obtained. The mixture was then allowed to warm to room temperature and stirred for an additional 12 hours, during which time the swelling of the beads occurred. Acetone was removed by distillation at 80° C.

The swollen beads were further grown by the addition of an ethyldivinylbenzene (310 g)-divinylbenzene (1:1.71) mixture containing 2.5 g dibenzoylperoxide as an initiator. Particle growth occurred with stirring, as determined by particle size measurements by means of light microscopy.

After completion of the swelling and growing stages, the reaction mixture was transferred to a separation funnel. The excess amount of the monomer separated from the layer containing the suspension of polymeric beads and was readily removed. The remaining suspension of beads was returned to the reactor and subjected to a stepwise increase in temperature (63° C. for about 7 hours, 73° C. for about 2 hours, and 83° C. for about 12 hours) leading to further increases in the degree of polymerization (>500). The pore size of beads prepared in this manner was below the detection limit of mercury porosimetry (<30 Å).

After drying, the dried beads (10 g) were suspended in 100 ml 1-chlorooctadecane and stirred (370 rpm) for 12 hours at 100° C. following an addition of 1 g of aluminum chloride. The reaction mixture was cooled to 80° C. and mixed with 150 ml of 4M hydrochloric acid. After 2 minutes of stirring, the reaction mixture was transferred to a separation funnel and overlaid by 300 ml of n-heptane. The phases were stirred mixed together and after subsequent separation of phases, the aqueous phase was removed and discarded. The remaining organic phase was washed two additional times with 200 ml of 1M hydrochloric acid and subsequently centrifuged at 5000 rpm. The separated beads were washed four times with 100 ml n-heptane and then two times with each of the following: 100 ml diethylether, 100 ml dioxane, and 100 ml methanol. Finally, the beads were dried.

Alternatively, the alkylation was carried out using tin chloride in place of aluminum chloride. Briefly, 100 ml 1-chlorooctadecane, 10 g poly(styrene/ethylstyrene/divinylbenzene) beads and 5 ml SnCl$_4$ were stirred for 12 hours. The mixture was cooled to room temperature, 100 ml of n-heptane was added and the mixture was then extracted with 4×300 ml water in a separation funnel until the aqueous phase was neutral (pH 7.0). Centrifugation was carried out for five minutes at 5000 rpm. The supernatant and 1-chlorooctadecane were discarded and water was removed as completely as possible. Washing with 2×150 ml n-heptane, 2×150 ml dioxane and with 2×150 ml methanol completed the procedure. Each one of the washing steps was followed by centrifugation at 5000 rpm. The alkylated beads were then dried at 60° C.

Alkylation of the aromatic rings of the polymer was verified by Fourier Transform Infrared spectroscopy (FTIR). The beads differed only slightly in size from each other. The mean value for the particle diameter was found to be 2.10 microns, with a standard deviation of 0.12 micron.

EXAMPLE 2

HPLC-Promoted-Denaturation of a Hybrid with a 2-Base Overhang

Liquid hybridization of two complementary oligonucleotides, oligo D, a 30-mer (SEQ ID NO:1) and oligo E (SEQ ID NO:2), a 32-mer with a 2 base overhang or "tail", was carried out by heating an equimolar mixture of oligonucleotide D and oligonucleotide E in 1×SSC buffer (0.2M NaCl, 0.165M trisodium citrate in water) to 90° C. for 10 minutes, followed by cooling to room temperature over a period of 30 minutes to produce a "D-E" hybrid with a two-base G-T overhang, located at positions 31-32 from the 5' end of oligo E.

The resulting hybrid-containing solution was then directly chromatographed on alkylated nonporous PS-DVB particles (as described in Example 1 above) packed into a stainless steel column (NPC18M HPLC Biopolymer column, 50×4.6 mm I.D., Serasep, Inc., Santa Clara, Calif.). Eluent A consisted of 0.1 M TEAA (triethylammonium acetate), pH 7.0 and Eluent B consisted of 0.1M TEAA, pH 7.0, 25% acetonitrile. The samples were eluted using a linear gradient profile of 25–50% Eluent B in 8 minutes, 50–80% Eluent B in 1 minute, and 80% Eluent B for 1 minute. The flow rate was 1 ml per minute. The column temperature was maintained at 40° C.

Chromatograms of samples of i) oligonucleotide probe D (FIG. 1A) and ii) oligonucleotide E (FIG. 1B) and iii) the resulting D-E hybrid having a two base overhang (FIG. 1C) are shown. Under the conditions employed and at a temperature of 40° C., partial denaturation of the duplex was observed (e.g., less than 100%), as indicated in FIG. 1C by a peak having a retention time between that of the 30-mer and the 32-mer, in addition to peaks corresponding to free probe (oligonucleotide D) and free template (oligonucleotide E).

The extent of denaturation as a function of increasing column temperature was observed by raising the temperature to 50° C. and re-running the above-described samples. The results are shown in FIGS. 2A-2C. As seen in FIG. 2C, raising the column temperature to 50° C. resulted in the complete denaturation of the D-E hybrid to produce a chromatogram cleanly separated into two distinct peaks corresponding to single stranded oligonucleotides D and E.

These results demonstrate the effect of increasing column temperature on the denaturation of short oligonucleotide homoduplexes with single stranded overhangs and further illustrate that such species (e.g., homoduplexes containing base overhangs) are detectable even under partially denaturing conditions (e.g., 40° C.).

EXAMPLE 3

HPLC-Promoted-Denaturation of a 43-mer Hybrid with a Single Base Mismatch

Oligonucleotide "C", a 43-mer having the sequence presented as SEQ ID NO:3 was prepared. Oligonucleotide "A" is a 43-mer that is complementary to oligonucleotide C with the exception of one base located ten bases from the 5' end of the strand (as shown at the bottom of FIGS. 3A-3C) and has the sequence presented as SEQ ID NO:4.

Liquid hybridization of the 43-mer oligonucleotides was carried out by heating an equimolar mixture of the oligonucleotides C and A in 1×SSC buffer solution to 90° C. for 10 minutes, followed by cooling to room temperature over a period of 30 minutes to produce a 43-mer hybrid (designated "C-A") with a single C-A base pair mismatch located at position 34 from the 5' end of oligo C.

The resulting hybrid-containing solution was then directly chromatographed on alkylated nonporous PS-DVB particles (as described in Example 1 above) packed into a stainless steel column (NPC18M HPLC Biopolymer column, 50×4.6 mm I.D., Serasep, Inc., Santa Clara, Calif.). Samples of each of the single stranded oligonucleotides C and A were injected onto the HPLC and chromatographed as controls. As in the previous example, eluent A consisted of 0.1M TEAA (triethylammonium acetate), pH 7.0 and Eluent B consisted of 0.1M TEAA, pH 7.0, 25% acetonitrile. The samples were eluted using a linear gradient profile of 30–50% Eluent B in 10 minutes, followed by 70% Eluent B for 1 minute, and a flow rate of 1 ml per minute. Two separate runs were performed at 40° C. and 51° C. to examine the effect of column temperature on denaturation and subsequent detection of a 43-mer duplex with a single base-pair mismatch. The results are shown in FIGS. 3A–3C and FIGS. 4A–4C, respectively.

At 51° C., complete denaturation of the duplex was observed, as evidenced by the detection of two single peaks with retention times corresponding to those of each of the single stranded oligonucleotides (FIG. 4C). At the lower temperature of 40° C., a single peak corresponding to the annealed oligonucleotides was observed (FIG. 3C).

These results illustrate the significance of column temperature in effecting complete denaturation of short duplex molecules containing a single base mismatch in the absence of an overhang. The complete denaturation was evidenced by the detection of the denatured single strands as distinct peaks in the resulting chromatogram, suggesting the utility of the method in separating oligonucleotides not only as a function of their size but also of their respective sequences.

EXAMPLE 4

A. Preparation of Polynucleotide Fragments Containing a Single Site Polymorphism The polynucleotides used in Examples 4–6 are described in Table 2. For ease of manipulation, the polynucleotide fragments were typically inserted into the SrfI 728 multiple cloning site of the pCR-ScriptSK(+) cloning vector (Stratagene, La Jolla, Calif.) and PCR amplified.

The 209 bp STS sY81 (Vollrath, et al.) was amplified from human genomic DNA and was cloned into the 2961 bp "PCR-SCRIPT" (SK+) plasmid vector (Stratagene, La Jolla, Calif.) at the Srf I site, resulting in a 3170 base pair plasmid construct.

Nucleotide position 168 within the 209 bp STS is polymorphic in humans, and is either an adenine (A) or guanidine (G) base (Seielstad, et al.). Both the A and G forms were initially subcloned from human genomic DNA. In the resulting plasmid construct, the inserted 209 bp STS sequence begins at vector nucleotide position 729. Correspondingly, in the 3170 bp clone, the single polymorphic locus is at nucleotide position 896.

Subsequent plasmid derivatives which differed only in nucleotide content at the immediate 896 position region were created by site-directed mutagenesis techniques using the A clone as the parental source.

Table 1 shows all possible nucleotide substitution heteroduplex mismatches formed from appropriate plasmid clones and subsequently detected by denaturing high performance liquid chromatography for exemplary size fragments up to 1.5 kb in length.

TABLE 1

| DUPLEX SPECIES | | | | |
|---|---|---|---|---|
| Clone # | A/T (1) | G/C (2) | T/A (3) | C/G (4) |
| A/T (1) | a/t | A/C + G/T | A/A + T/T | A/G + C/T |
| G/C (2) | G/T + A/C | g/c | G/A + T/C | G/G + C/C |
| T/A (3) | T/T + A/A | T/C + G/A | t/a | T/G + C/A |
| C/G (4) | C/T + A/G | C/C + G/G | C/A + T/G | c/g |

Lower case = homoduplexes
Upper case = heteroduplexes

TABLE 2

| POLYNUCLEOTIDES | | | |
|---|---|---|---|
| | Sequence or Source of DNA | Forward Primer/ (Position of 5' end in 2961 bp clone) | Reverse Primer/ (Position of 5' end in 2961 bp clone) |
| homo-A-209 | SEQ ID NO:5 SEQ ID NO:6 | SEQ ID NO:9 | SEQ ID NO:10 |
| homo-G-209 | SEQ ID NO:7 SEQ ID NO:8 | SEQ ID NO:9 | SEQ ID NO:10 |
| homo-A-439 | plasmid clone | SEQ ID NO:26 (599) | SEQ ID NO:27 (828) |
| homo-G-439 | plasmid clone | SEQ ID NO:26 (599) | SEQ ID NO:27 (828) |
| homo-A-1 kb | plasmid clone | SEQ ID NO:28 (318) | SEQ ID NO:29 (1108) |
| homo-G-1 kb | plasmid clone | SEQ ID NO:28 (318) | SEQ ID NO:29 (1108) |
| homo-A-1.5 kb | plasmid clone | SEQ ID NO:24 (68) | SEQ ID NO:25 (1358) |
| homo-G-1.5 kb | plasmid clone | SEQ ID NO:24 (68) | SEQ ID NO:25 (1358) |

B. Denaturation/Reannealing of 209-mer Homoduplexes Formation and Detection of 209-mer Heteroduplexes Synthetic oligonucleotide single stranded PCR primers 209-F (SEQ ID NO:9) and 209-R (SEQ ID NO:10) were used to amplify the 209 base pair STS, sY81, from either human male genomic DNA or from plasmid clones containing either allelic (A or G) form of the polymorphic STS.

Double-stranded DNA homoduplex A, "homo-A-209", a 209-base pair fragment was composed of two complementary 209-base fragments, polynucleotide 1 (SEQ ID NO:5) and polynucleotide 2 (SEQ ID NO:6). Double stranded DNA homoduplex G, "homo-G-209", a 209-base pair fragment identical in sequence to homo-A-209 with the exception of one base pair (a G-C substituted for A-T present in homo-A-209) was composed of polynucleotide 3 (SEQ ID NO:7) and complementary polynucleotide 4 (SEQ ID NO:8). Polynucleotide 3 was identical in sequence to polynucleotide 1, with the exception of a guanosine at position 168 from the 5' end of polynucleotide 3, in comparison to an adenosine at the analogous position in polynucleotide 1. In a similar fashion, polynucleotide 4 was identical in sequence to polynucleotide 2, with the exception of a cytosine at position 42 from the 5' end replacing a thymidine in the same position in polynucleotide 2.

The double stranded oligonucleotides homo-A-209 and homo-G-209 were subjected to denaturation and reannealing under the following conditions in a Perkin Elmer 9600 thermal cycler: 95° C. for 3 minutes, followed by cooling from 95° C. to 65° C. at a rate of 1° C. per minute (e.g., over a period of 30 minutes), followed by sample storage at 6° C. A schematic representation of the products formed by denaturing the above 209-mer homoduplexes followed by reannealing is provided in FIG. 5. The resulting mixture of products, containing original homoduplexes homo-A-209 and homo-G-209 and newly formed heteroduplexes hetero-AC-209 and hetero-GT-209 were then analyzed by IP-RP-HPLC. Hetero-AC-209 represents the double stranded product formed by annealing oligonucleotides 1 and 4, and contains a single base pair A-C mismatch at position 168 relative to oligo 1. Hetero-GT-209 represents the double stranded product formed by annealing oligonucleotides 2 and 3, and contains a single base pair G-T mismatch at position 168 relative to oligo 2.

Samples of each of homo-A-209, homo-G-209, and the resulting heteroduplexes formed by denaturation and naturation of homo-A-209 and homo-G-209 were then directly chromatographed on alkylated nonporous PS-DVB particles (as described above) packed into a stainless steel column (NPC18M HPLC Biopolymer column, 50×4.6 mm I.D., Serasep, Inc., Santa Clara, Calif.). Eluent A consisted of 0.1M TEAA (triethylammonium acetate), pH 7.0 and Eluent B consisted of 0.1M TEAA, pH 7.0, in 25 % acetonitrile. The samples were eluted using a linear gradient profile of 37–63% Eluent B in 5.5 minutes, followed by 90% Eluent B for 1.5 minutes, at a flow rate of 1 ml per minute (UV detection, 254 nm). Two separate runs were performed at 50° C. and 54° C. to optimize the effect of column temperature on separation of the product mixture components, as shown in FIGS. 6A–6C and FIGS. 7A–7C, respectively.

At a less stringent column temperature of 50° C., separation/detection of the product mixture containing homo-A-209, homo-G-209, hetero AC-209, and hetero-GT-209 was not achieved (FIG. 6C). However, upon raising the column temperature to 54° C., the two homoduplex products were clearly separated from the heteroduplexes, which eluted from the column slightly faster than did the homoduplexes.

In contrast to shorter double stranded DNA fragments having less than about 70 base pairs and containing a single base pair mismatch (e.g., Example 3), larger DNA fragments are only partially denatured using the optimized chromatographic conditions of the present invention, resulting in the formation of a "bubble" at the site of the base-pair mismatch. This partial denaturation or bubble causes a shift towards shorter retention times and allows the separation of heteroduplexes containing a single base pair mismatch from homoduplexes of the same size, as illustrated in FIG. 7C.

Further to this point, FIGS. 10A–10C illustrate the sensitivity and resolving power of the method as a function of column temperature for samples of homo-A-209 and homo-G-209, subjected to denaturation and reannealing conditions, to produce a mixture containing homo-A-209, homo-G-209, hetero-AC-209, and hetero-GT-209. As seen in FIGS. 10A–C, at 50° C. the mixture elutes as a single peak, with resolution improving at a heightened column temperature of 52° C., and resulting in base line separation of the heteroduplexes from the homoduplex products at an optimized column temperature of 56° C.

In summary, the above results show the effective separation of larger nucleic acid duplexes (e.g. over 200 base pairs) containing a single base pair mismatch from homoduplexes of about the same size by partial denaturation of the heteroduplexes using the denaturing HPLC conditions described herein, leading to shorter retention times.

EXAMPLE 5

Denaturation/Reannealing of 439-mer Homoduplexes Formation and Detection of 439-mer Heteroduplexes In order to examine the sensitivity of the HPLC detection method of the invention, an experiment identical to that described in Example 4 above was carried out with two different DNA homoduplexes each containing 439 base pairs.

The reagents were obtained by amplifying the fragments from the appropriate plasmid (A or G) constructs using synthetic single strand oligonucleotide PCR primers 439-F (SEQ ID NO:26) and 439-R (SEQ ID NO:27).

The 439-base pair homoduplex A, designated as homo-A-439, was obtained by annealing polynucleotide 5 with polynucleotide 6. A 439-base pair homoduplex G, designated as homo-G-439, was obtained by annealing polynucleotide 7 with polynucleotide 8. Denaturation and reannealing were carried out as described above, generating a mixture containing homo-A-439, homo-G-439, and two resulting heteroduplex species.

The resulting IP-RP-HPLC chromatograms for both homo-A-439 and homo-G-439 as well as for the sample obtained from denaturing and subsequent reannealing of homo-A-439 and homo-G-439 are shown in FIGS. 8A–8C, respectively. The column, column packing, composition of Eluent A and Eluent B, linear gradient, as well as the flow rate and detector wavelength are the same as those employed in Example 4. The separation was carried out at a column temperature of 56° C. As seen in FIG. 8C, detection of the 439-mer heteroduplexes present in a sample also containing two 439-mer homoduplexes is achieved under the conditions employed, as evidenced by the peaks having shorter retention times and indicated by an arrow.

The samples were also chromatographed at a column temperature of 50° C., however, separation of the components of the reaction mixture containing both heteroduplex and homoduplex products was not achieved at the lower column temperature (not shown), since the products co-elute as a single peak.

These results further support the general applicability of the method in separating and detecting single base pair mismatches in heteroduplexes containing nearly 500 base pairs and further demonstrate the effect of column temperature in effecting at least partial denaturation of heteroduplex molecules in a sample containing both heteroduplexes and homoduplexes, as suggested by peaks (corresponding to the heteroduplex) having shorter retention times.

EXAMPLE 6

A. Denaturation/Reannealing of 1000-Base Pair Homoduplexes: Formation and Detection of 1000-Base Pair Heteroduplexes To further investigate the separation capabilities of the present method, an experiment similar to that described in Example 5 above was carried out with two different DNA homoduplexes each 1 kilobase in length.

The 1 kilobase products were generated by amplifying from the appropriate plasmid using synthetic single strand oligonucleotide PCR primers 1kb-F (SEQ ID NO:28) and 1kb-R (SEQ ID NO:29).

The 1000-base pair homoduplex A, designated as homo-A-1kb, was obtained by annealing polynucleotide 9 with polynucleotide 10. 1000-base pair homoduplex G, designated as homo-G-1kb, was obtained in a similar manner. Denaturation and reannealing were carried out as described above to produce a sample containing homoduplexes homo-A-1kb and homo-G-1kb as well as the two heteroduplexes, hetero-AC-1kb and hetero-GT-1kb.

The resulting IP-RP-HPLC chromatograms for both homo-A-1kb and homo-G-1kb as well as for the sample obtained from denaturing and subsequent reannealing of homo-A-1kb and homo-G-1kb are shown in FIGS. 9A–9C, respectively. The column, column packing, and composition of Eluent A and Eluent B were the same as those employed in Examples 4 and 5. A linear gradient of 40%–70% B in 7 minutes, followed by an increase to 90% B in 1.5 minutes was used to elute the products. A flow rate of 1 ml/minutes and a detector wavelength of 256 nm was employed. The separation was carried out at a column temperature of 56° C. and resulted in the detection of 1-kilobase heteroduplexes containing only a single base pair mismatch in a sample also containing 1-kb homoduplexes.

As in the previous examples, the samples were also chromatographed at a column temperature of 50° C., however, separation/detection of the 1-kilobase heteroduplexes in a sample also containing 1-kilobase homoduplex products was not achieved at the lower column temperature (not shown). At the lower column temperature, the mixture of homo- and heteroduplex products co-elute and are detected as a single peak.

The above results demonstrate the utility of the method in detecting single base pair mismatches in heteroduplexes up to 1 kilobase in size under chromatographic conditions similar to those used in the separation of shorter nucleic acid fragments, suggesting the general applicability of the method. The results further suggest the potential for detecting single base pair mismatches in duplexes larger than 1 kilobase in size.

B. Denaturation/Reannealing of 1500-Base Pair Homoduplexes: Formation and Detection of 1500-Base Pair Heteroduplexes In a similar fashion to Example 6A described above, 1.5 kilobase heteroduplex molecules containing a single base pair mismatch were separated using the denaturing HPLC method of the present invention.

The 1.5 kb fragment was amplified essentially as described above using primers SEQ ID NO:24 (forward) and SEQ ID NO:25 (reverse). The 1.5 kb A form sequence of polynucleotide 11 was annealed with polynucleotide 12 to create a 1.5 kb homoduplex, homo-A-1.5 kb. A similar 1.5 kb G form sequence was also generated from the complementary polynucleotides 13 and 14, homo-G-1.5 kb. Following mixing, denaturing and reannealing the 1.5 kb homo A and G duplexes, the single base mismatch of the resulting heteroduplex molecules was at position 829 from the 5' end of polynucleotides 11 and 13.

The separation was effected at a pH of 7.5. The elution was carried out using a Gynkotek low-pressure gradient HPLC system (Gynkotek, Germering, Germany) at a temperature of 57° C. and a flow rate of 1 ml/minute. A binary gradient system was employed (with components as described above), using a linear gradient profile of 62–71% Eluent B in 5 minutes. The chromatograms are shown in FIGS. 12A–12C, with FIG. 12C illustrating separation of the 1.5 kb heteroduplex molecules from the corresponding homoduplexes. The results suggest the potential for detecting single base mismatches in duplexes up to 2 kilobase in size using the present method.

EXAMPLE 7

General Amplification Method

For initial template DNA screening reactions, a mixture containing 55 µl Boehringer Mannheim 10× PCR reaction buffer (100 mM Tris-HCl, 15 mM $MgCl_2$, pH 8.3), 2.75 µl forward primer 0 µM), 2.75 µl reverse primer (20 µM), 22.0 µl dNTP mix (1.25 mM each), 2.2 µl Taq DNA polymerase and 459.8 µl water was prepared using aerosol barrier filter pipette tips for the dispensing of reagents. Aliquots (99 µl each) were dispensed in each of five PCR reaction tubes, to each of which was added 1 µl of template DNA (250 ng). Initial screening was typically carried out on DNA templates derived from 3 males and 1 female, in addition to one water control.

PCR amplifications were carried out using a "touchdown" protocol, as has been previously described (Don, et al.). The thermal cycling conditions employed (Seielstad, et al.) were: 94° C. for 1 minute (1 cycle); 94° C. for 20 seconds, 63° C. to 56.5° C. in 1 minute (e.g., 0.5° C. decrease per cycle), 72° C. for 1 minute (14 cycles); 94° C. for 20 seconds, 56° C. for 45 seconds, 72° C. for 1 minute (20 cycles); 72° C. for 5 minutes (1 cycle); followed by storage at 6° C.

Following the completion of PCR cycling, 10 µl aliquots were analyzed on 1.5% "TBE" (tris borate-EDTA) agarose gel using a 123 base pair-sized standard ladder. Loading wells were created using 1 mm thick combs. Once PCR conditions were optimized to generate specific STS fragments, additional individual DNA samples were amplified.

EXAMPLE 8

Polymorphic Site Identification on the Human y Chromosome

Y-chromosome specific STSs (Vollrath, et al.) were amplified using touchdown PCR (Don, et al.). Amplification primers for STS amplification were obtained from Research Genetics, Inc. (Huntsville, Ala.). The PCR reaction products were analyzed by agarose gel electrophoresis and purified using Qiagen "QIAQUICK" spin columns. The amplified STSs were sequenced using the amplification oligonucleotides as sequencing primers and DyeDeoxy Terminator sequencing reagents (Applied Biosystems Division, Perkin Elmer, Foster City, Calif.) using standard manufacturer's protocols. The products of the sequencing reactions were purified by Centri-Sep spin columns (Princeton Separations, Adelphia, N.J.), followed by analysis on a 373A DNA sequencer (Applied Biosystems Division, Perkin Elmer, Foster City, Calif.).

Y-chromosomal DNA samples obtained from 22 male individuals of diverse geographical origins (Africa (5), Asia (3), Oceania (3), Europe (3), and America (8)) were comparatively sequenced using the method of the present invention to identify polymorphic sites located on locus DYS199. Polymorphic site identification was confirmed by subsequent conventional sequencing techniques.

Amplification products from an arbitrarily chosen reference control SY103 STS sample were separately mixed with amplification products from each of the other populations examined. The same reference strand (derived from an African pygmy individual) was used as a control for each of the populations studied. Each set of mixed, amplified fragments were heat denatured and allowed to reanneal, as described in previous examples.

The resulting sample mixtures (3–20 µl volume) were then injected onto a column containing an alkylated stationary phase (NPC18M, No. 6210546, 50×4.6 mm, I.D., Serasep, Inc., Santa Clara, Calif.) conditioned with an ion pairing agent. Eluent A consisted of 0.1M TEAA, at pH 7.0, while Eluent B was a mixture of 0.1M TEAA at pH 7.0 in 25% acetonitrile. A binary gradient system of 37–63% Eluent B in 5.5 minutes, followed by an increase to 90% Eluent B in 1.5 minutes was used to elute the samples at a flow rate of 1 ml/min. The column temperature was maintained at 56° C.

Exemplary chromatograms are shown in FIGS. 11A and 11B, illustrating HPLC traces of (i) a sample containing only homoduplex molecules derived from samples of Italian origin (FIG. 11A), (ii) in comparison with samples of native South American origin, indicating the presence of heteroduplexes.

The nature of the base pair mismatch was then verified by DNA sequencing. In greater than 90% of the samples of native South American origin, a single polymorphic nucleotide substitution, a C-to-T transition, was observed at base position 181 of locus DYS199.

Genotyping of the DYS199 locus (corresponding to the 241-bp sY103 STS) was performed by allele specific PCR. In carrying out allele-specific PCR, two amplification reactions were performed for each sample in which the DYS199 forward primer (SEQ ID NO:13) was combined with one of two allele specific reverse primers, the C-specific reverse primer (SEQ ID NO:14) or the T-specific reverse primer (SEQ ID NO:15).

Each 15 μl allele reaction contained 50 ng of genomic DNA, 5 pmol of each primer, 100 μM each of dNTP, 1.5 mM MgCl$_2$, 10 mM Tris pH 9.0, 50 mM KCl, and 0.375 unit Taq polymerase. Thirty cycles of allele specific PCR were performed using the following two step regime: 94° C. for 30 s and 61° C. for 20 s. The reaction products were analyzed on an ethidium bromide stained agarose gel and the specific 209 bp product was visualized by UV to determine allelic state. Positive controls of both C and T allele individuals (having genotypes previously confirmed by sequencing) were included in all allele specific PCR genotyping experiments.

Polymorphisms have also been identified at the following sites along the Y-chromosome by comparative sequencing using denaturing HPLC as described above.

TABLE 3

| Locus* | Forward Primer | Reverse Primer | Single Base Conversion | Polymorphism assoc. w/ Regional Populations |
|--------|---------------|----------------|-----------------------|---------------------------------------------|
| DYS 198 | SEQ ID NO:16 | SEQ ID NO:17 | T to G | S. Africa |
| DYS 234 | SEQ ID NO:18 | SEQ ID NO:19 | A to G | Oceania |
| DYS 253 | SEQ ID NO:20 | SEQ ID NO:21 | C to G | China |
| DYS 263 | SEQ ID NO:22 | SEQ ID NO:23 | G to T | Japan |

*Vollrath, 1992.

Further human or non-human nucleic acid polymorphisms can be identified within either haploid genomes such as the Y chromosome or diploid genomes such as autosomal chromosomes using essentially the same method as described above.

While the invention has been described with reference to specific methods and embodiments, it will be appreciated that various modifications and changes may be made without departing from the invention.

It is claimed:

1. A chromatographic method for separating heteroduplex and homoduplex DNA molecules in a mixture, comprising:

applying the mixture to a stationary reverse phase support, eluting the heteroduplex and homoduplex molecules of said mixture with a mobile phase containing an ion-pairing reagent and an organic solvent, where said eluting is carried out under conditions effective to at least partially denature said heteroduplexes and where said eluting results in the separation of said heteroduplexes from said homoduplexes.

2. The method of claim 1, where the stationary support is composed of an alkylated base material, said base material selected from the group consisting of silica, alumina, zirconia, polystyrene, polyacrylamide, and styrene-divinyl copolymers.

3. The method of claim 1, where the mobile phase contains an ion-pairing agent selected from the group consisting of lower alkyl primary, secondary, and tertiary amines, lower trialkylammonium salts and lower quaternary ammonium salts.

4. The method of claim 3, where the mobile phase is triethylamine.

5. The method of claim 1, where the mobile phase contains an organic solvent selected from the group consisting of methanol, ethanol, acetonitrile, ethyl acetate, and 2-propanol.

6. The method of claim 1, where the mobile phase contains less than about 40% by volume of said organic solvent.

7. The method of claim 1, where said eluting is carried out at a temperature between about 50° and 65° C.

8. The method of claim 2, where the base material is a styrene-divinyl copolymer composed of a styrene monomer selected from the group consisting of styrene, alkyl-substituted styrene, α-methylstyrene and alkyl substituted α-methylstyrene and a divinyl monomer selected from the group consisting of divinylbenzene and divinylbutadiene.

9. The method of claim 2, where the surface of said base material is alkylated with hydrocarbon chains containing from 4–18 carbon atoms.

10. The method of claim 1, where the mobile phase contains greater than about 60% by volume of an aqueous solution of the ion-pairing agent at a concentration between about 0.05 and 1.0 molar.

11. The method of claim 3, where said ion-pairing agent is triethylammonium acetate.

12. The method of claim 1, where said stationary phase is a C-18 alkylated polystyrene-divinylbenzene copolymer support, and where the ion-pairing reagent contained in the mobile phase is triethylammonium acetate and the organic solvent is acetonitrile.

13. The method of claim 12, where said eluting is carried out at a temperature between about 50°–65° C.

14. The method of claim 12, where said eluting is carried out at about 56° C.

15. The method of claim 14, where the mobile phase contains greater than about 60% by volume of an aqueous solution of triethylammonium acetate and less than about 40% by volume of acetonitrile.

16. The method of claim 1, where said eluting is carried out a pH between 7.0 and 9.0.

17. The method of claim 16, where said eluting is carried out at pH 7.5.

18. The method of claim 13, where said eluting is carried out at pH 7.5.

19. The method of claim 1, where prior to said applying step the DNA molecules are amplified using the polymerase chain reaction and the amplified DNA molecules denatured and renatured to form a mixture of heteroduplex and homoduplex DNA molecules.

20. The method of claim 19, where prior to amplification, the DNA molecules are obtained by reverse transcription.

* * * * *

UNITED STATES PATENT AND TRADEMARK OFFICE
CERTIFICATE OF CORRECTION

PATENT NO. : 5,795,976
DATED : August 18, 1998
INVENTOR(S) : Oefner, P.J., et al.

It is certified that error appears in the above-indentified patent and that said Letters Patent is hereby corrected as shown below:

In column 1, line 7, insert:

--This work was supported in part by National Institutes of Health Grant GM 28428. Accordingly, the United States Government has certain rights in this invention.--

Signed and Sealed this

Twenty-seventh Day of July, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: OLIGO D- 30MER ( x i ) SEQUENCE DESCRIPTION: SEQ ID NO:1:

GAGGATGAAG AAGACTCCAG GACTCTAGAG            30

( 2 ) INFORMATION FOR SEQ ID NO:2:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:

(C) INDIVIDUAL ISOLATE: OLIGO E - 32MER (x i) SEQUENCE DESCRIPTION: SEQ ID NO:2:

CTCTAGAGTC CTGGAGTCTT CTTCATCCTC GT                                32

(2) INFORMATION FOR SEQ ID NO:3:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: OLIGO C - 43MER (x i) SEQUENCE DESCRIPTION: SEQ ID NO:3:

GGAAGGACTG GACTGACTCC AAGTACTAGC TGACCGTGAA GGC                    43

(2) INFORMATION FOR SEQ ID NO:4:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: DNA (v i) ORIGINAL SOURCE:
        (C) INDIVIDUAL ISOLATE: OLIGO-A-43- MER (x i) SEQUENCE DESCRIPTION: SEQ ID NO:4:

GCCTTCACGA TCAACTAGTA CTTGGAGTCA GTCCAGTCCT TCC                    43

(2) INFORMATION FOR SEQ ID NO:5:

(i) SEQUENCE CHARACTERISTICS:
        (A) LENGTH: 209 base pairs
        (B) TYPE: nucleic acid
        (C) STRANDEDNESS: single
        (D) TOPOLOGY: linear (i i) MOLECULE TYPE: DNA (genomic)

(v i) ORIGINAL SOURCE:
        (C) INDIVIDUAL ISOLATE: HOMO-A-209, POLYNUCLEOTIDE 1

(x i) SEQUENCE DESCRIPTION: SEQ ID NO:5:

AGGCACTGGT CAGAATGAAG TGAATGGCAC ACAGGACAAG TCCAGACCCA GGAAGGTCCA    60

GTAACATGGG AGAAGAACGG AAGGAGTTCT AAAATTCAGG GCTCCCTTGG GCTCCCTGT    120

TTAAAAATGT AGGTTTTATT ATTATATTTC ATTGTTAACA AAAGTCCATG AGATCTGTGG   180

AGGATAAAGG GGGAGCTGTA TTTTCCATT                                     209

(2) INFORMATION FOR SEQ ID NO:6:

(i) SEQUENCE CHARACTERISTICS:
        (A) LENGTH: 209 base pairs
        (B) TYPE: nucleic acid
        (C) STRANDEDNESS: single
        (D) TOPOLOGY: linear (i i) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: HOMO-A- 209/POLYNUCLEOTIDE 2

(xi) SEQUENCE DESCRIPTION: SEQ ID NO:6:

| | | | | | |
|---|---|---|---|---|---|
| AATGGAAAAT | ACAGCTCCCC | CTTTATCCTC | CACAGATCTC | ATGGACTTTT | GTTAACAATG | 60 |
| AAATATAATA | ATAAAACCTA | CATTTTTAAA | CAGGGGAGCC | CAAGGGAGCC | CTGAATTTTA | 120 |
| GAACTCCTTC | CGTTCTTCTC | CCATGTTACT | GGACCTTCCT | GGGTCTGGAC | TTGTCCTGTG | 180 |
| TGCCATTCAC | TTCATTCTGA | CCAGTGCCT | | | | 209 |

(2) INFORMATION FOR SEQ ID NO:7:

(i) SEQUENCE CHARACTERISTICS:
(A) LENGTH: 209 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: HOMO-G- 209/POLYNUCLEOTIDE 3

(xi) SEQUENCE DESCRIPTION: SEQ ID NO:7:

| | | | | | |
|---|---|---|---|---|---|
| AGGCACTGGT | CAGAATGAAG | TGAATGGCAC | ACAGGACAAG | TCCAGACCCA | GGAAGGTCCA | 60 |
| GTAACATGGG | AGAAGAACGG | AAGGAGTTCT | AAAATTCAGG | GCTCCCTTGG | GCTCCCTGT | 120 |
| TTAAAAATGT | AGGTTTTATT | ATTATATTTC | ATTGTTAACA | AAAGTCCGTG | AGATCTGTGG | 180 |
| AGGATAAAGG | GGGAGCTGTA | TTTTCCATT | | | | 209 |

(2) INFORMATION FOR SEQ ID NO:8:

(i) SEQUENCE CHARACTERISTICS:
(A) LENGTH: 209 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: HOMO-G- 209/POLYNUCLEOTIDE 4

(xi) SEQUENCE DESCRIPTION: SEQ ID NO:8:

| | | | | | |
|---|---|---|---|---|---|
| AATGGAAAAT | ACAGCTCCCC | CTTTATCCTC | CACAGATCTC | ACGGACTTTT | GTTAACAATG | 60 |
| AAATATAATA | ATAAAACCTA | CATTTTTAAA | CAGGGGAGCC | CAAGGGAGCC | CTGAATTTTA | 120 |
| GAACTCCTTC | CGTTCTTCTC | CCATGTTACT | GGACCTTCCT | GGGTCTGGAC | TTGTCCTGTG | 180 |
| TGCCATTCAC | TTCATTCTGA | CCAGTGCCT | | | | 209 |

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (vi) ORIGINAL SOURCE:
(C) INDIVIDUAL ISOLATE: 209-MER FORWARD PRIMER ( x i ) SEQUENCE DESCRIPTION: SEQ ID NO:9:

AGGCACTGGT CAGAATGAAG                                                                    20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( v i ) ORIGINAL SOURCE:
        ( C ) INDIVIDUAL ISOLATE: REVERSE PRIMER FOR 209-MER ( x i ) SEQUENCE DESCRIPTION: SEQ ID NO:10:

AATGGAAAAT ACAGCTCCCC                                                                    20

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( v i ) ORIGINAL SOURCE:
        ( C ) INDIVIDUAL ISOLATE: FORWARD PRIMER FOR BETA MAJOR GLOBIN
            PROMOTER ( x i ) SEQUENCE DESCRIPTION: SEQ ID NO:11:

CTGGCACGCG CTGGACGCG                                                                     19

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( v i ) ORIGINAL SOURCE:
        ( C ) INDIVIDUAL ISOLATE: REVERSE PRIMER FOR BETA MAJOR GLOBIN
            PROMOTER ( x i ) SEQUENCE DESCRIPTION: SEQ ID NO:12:

CTCAGCATCA GTCAGGTGC                                                                     19

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( v i ) ORIGINAL SOURCE:
        ( C ) INDIVIDUAL ISOLATE: DYS199 FORWARD PRIMER ( x i ) SEQUENCE DESCRIPTION: SEQ ID NO:13:

TAATCAGTCT CCTCCCAGCA                                                                    20

( 2 ) INFORMATION FOR SEQ ID NO:14:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: DNA ( v i ) ORIGINAL SOURCE:
   ( C ) INDIVIDUAL ISOLATE: C-SPECIFIC REVERSE PRIMER FOR DYS199

( x i ) SEQUENCE DESCRIPTION: SEQ ID NO:14:

GGTACCAGCT CTTCCTAATT G     21

( 2 ) INFORMATION FOR SEQ ID NO:15:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( v i ) ORIGINAL SOURCE:
      ( C ) INDIVIDUAL ISOLATE: T-SPECIFIC REVERSE PRIMER FOR DYS199

( x i ) SEQUENCE DESCRIPTION: SEQ ID NO:15:

GGTACCAGCT CTTCCTAATT A     21

( 2 ) INFORMATION FOR SEQ ID NO:16:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( v i ) ORIGINAL SOURCE:
      ( C ) INDIVIDUAL ISOLATE: DYS198 FORWARD PRIMER ( x i ) SEQUENCE DESCRIPTION: SEQ ID NO:16:

CACTACCACA TTTCTGGTTG G     21

( 2 ) INFORMATION FOR SEQ ID NO:17:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA ( v i ) ORIGINAL SOURCE:
      ( C ) INDIVIDUAL ISOLATE: DYS198 REVERSE PRIMER ( x i ) SEQUENCE DESCRIPTION: SEQ ID NO:17:

CGCTGAGTCC ATTCTTTGAG     20

( 2 ) INFORMATION FOR SEQ ID NO:18:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA ( v i ) ORIGINAL SOURCE:
( C ) INDIVIDUAL ISOLATE: DYS198 REVERSE PRIMER ( x i ) SEQUENCE DESCRIPTION: SEQ ID NO:18:

CGCTGAGTCC ATTCTTTGAG    20

( 2 ) INFORMATION FOR SEQ ID NO:19:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( v i ) ORIGINAL SOURCE:
( C ) INDIVIDUAL ISOLATE: DYS234 REVERSE PRIMER ( x i ) SEQUENCE DESCRIPTION: SEQ ID NO:19:

TGCAGAACAT TTGTACTGTT CC    22

( 2 ) INFORMATION FOR SEQ ID NO:20:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( v i ) ORIGINAL SOURCE:
( C ) INDIVIDUAL ISOLATE: DYS253 FORWARD PRIMER ( x i ) SEQUENCE DESCRIPTION: SEQ ID NO:20:

ACTGTGAGCG AGCTGAAAAT    20

( 2 ) INFORMATION FOR SEQ ID NO:21:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( v i ) ORIGINAL SOURCE:
( C ) INDIVIDUAL ISOLATE: DYS253 REVERSE PRIMER ( x i ) SEQUENCE DESCRIPTION: SEQ ID NO:21:

GCAGCCTTGT GAACCAATTA    20

( 2 ) INFORMATION FOR SEQ ID NO:22:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( v i ) ORIGINAL SOURCE:
( C ) INDIVIDUAL ISOLATE: DYS263 FORWARD PRIMER ( x i ) SEQUENCE DESCRIPTION: SEQ ID NO:22:

CCCACCCACT TCAGTATGAA    20

( 2 ) INFORMATION FOR SEQ ID NO:23:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( v i ) ORIGINAL SOURCE:
( C ) INDIVIDUAL ISOLATE: DYS263 REVERSE PRIMER ( x i ) SEQUENCE DESCRIPTION: SEQ ID NO:23:

AGGCTGACAG ACAAGTCCAC  20

( 2 ) INFORMATION FOR SEQ ID NO:24:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( v i ) ORIGINAL SOURCE:
( C ) INDIVIDUAL ISOLATE: FORWARD PRIMER FOR 1.5 KB DUPLEXES ( x i ) SEQUENCE DESCRIPTION: SEQ ID NO:24:

AACCAATAGG CCGAAATCGG  20

( 2 ) INFORMATION FOR SEQ ID NO:25:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( v i ) ORIGINAL SOURCE:
( C ) INDIVIDUAL ISOLATE: REVERSE PRIMER FOR 1.5 KB DUPLEXES ( x i ) SEQUENCE DESCRIPTION: SEQ ID NO:25:

AAGCGGCAGG GTCGGAAC  18

( 2 ) INFORMATION FOR SEQ ID NO:26:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( v i ) ORIGINAL SOURCE:
( C ) INDIVIDUAL ISOLATE: 439-MER FORWARD PRIMER ( x i ) SEQUENCE DESCRIPTION: SEQ ID NO:26:

TGTAAAACGA CGGCCAGT  18

( 2 ) INFORMATION FOR SEQ ID NO:27:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear (i i) MOLECULE TYPE: DNA (v i) ORIGINAL SOURCE:
 (C) INDIVIDUAL ISOLATE: 439-MER REVERSE PRIMER (x i) SEQUENCE DESCRIPTION: SEQ ID NO:27:

CAGGAAACAG CTATGACG    18

(2) INFORMATION FOR SEQ ID NO:28:

(i) SEQUENCE CHARACTERISTICS:
 (A) LENGTH: 20 base pairs
 (B) TYPE: nucleic acid
 (C) STRANDEDNESS: single
 (D) TOPOLOGY: linear (i i) MOLECULE TYPE: DNA (v i) ORIGINAL SOURCE:
 (C) INDIVIDUAL ISOLATE: 1 KB FORWARD PRIMER (x i) SEQUENCE DESCRIPTION: SEQ ID NO:28:

GACGGGGAAA GCCGGCGAAC    20

(2) INFORMATION FOR SEQ ID NO:29:

(i) SEQUENCE CHARACTERISTICS:
 (A) LENGTH: 20 base pairs
 (B) TYPE: nucleic acid
 (C) STRANDEDNESS: single
 (D) TOPOLOGY: linear (i i) MOLECULE TYPE: DNA (v i) ORIGINAL SOURCE:
 (C) INDIVIDUAL ISOLATE: 1 KB REVERSE PRIMER (x i) SEQUENCE DESCRIPTION: SEQ ID NO:29:

GCCTTTGAGT GAGCTGATAC    20